United States Patent
Falco et al.

(10) Patent No.: US 7,634,304 B2
(45) Date of Patent: Dec. 15, 2009

(54) METHOD AND APPARATUS FOR LESION LOCALIZATION, DEFINITION AND VERIFICATION

(75) Inventors: Tony Falco, La Prairie (CA); Dimitre Hristov, Montreal (CA)

(73) Assignee: McGill University, Montreal, Quebec (CA)

( * ) Notice: Subject to any disclaimer, the term of this patent is extended or adjusted under 35 U.S.C. 154(b) by 278 days.

(21) Appl. No.: 10/343,336

(22) PCT Filed: Jul. 31, 2001

(86) PCT No.: PCT/CA01/01113

§ 371 (c)(1),
(2), (4) Date: Aug. 25, 2003

(87) PCT Pub. No.: WO02/09588

PCT Pub. Date: Feb. 7, 2002

(65) Prior Publication Data

US 2004/0034301 A1 Feb. 19, 2004

(30) Foreign Application Priority Data

Aug. 1, 2000 (CA) .................................. 2314794

(51) Int. Cl.
*A61B 8/00* (2006.01)
(52) U.S. Cl. ....................... 600/424; 600/407; 600/426; 600/440; 600/442; 600/443
(58) Field of Classification Search ................. 600/417, 600/424, 425, 429, 439, 443, 459, 407, 428, 600/440, 442; 606/130
See application file for complete search history.

(56) References Cited

U.S. PATENT DOCUMENTS

| 3,082,322 A | 3/1963 | Koerner et al. ............. 250/61.5 |
| 3,777,124 A | 12/1973 | Pavkovich .................. 235/151 |
| 3,987,281 A | 10/1976 | Hodes ..................... 235/151.3 |

(Continued)

FOREIGN PATENT DOCUMENTS

EP  0 647 457 A1  4/1995

(Continued)

OTHER PUBLICATIONS

Besl et al., *A Method for Registration of 3d Shapes*, IEEE Transactions on Pattern Analysis and Machine Intelligence 14(2):239-256 (1992).

(Continued)

*Primary Examiner*—Brian Casler
*Assistant Examiner*—Baisakhi Roy
(74) *Attorney, Agent, or Firm*—Goodwin Procter LLP

(57) ABSTRACT

A method and apparatus for lesion or organ definition for the purpose of radiation treatment planning localization and treatment position verification. The apparatus uses a combination of an ultrasound imaging system and a diagnostic imaging system to acquire localization ultrasound images referenced in the coordinate space of the diagnostic imaging system through the use of a position sensing system. The method compares the location of the lesion in the localization ultrasound images with the position of the lesion in ultrasound images taken while the patient lies on the treatment table of a therapy treatment unit, suggests corrective measures to place the lesion in its intended treatment position and executes the correction upon confirmation from qualified personnel.

15 Claims, 21 Drawing Sheets

U.S. PATENT DOCUMENTS

| | | | |
|---|---|---|---|
| 3,991,310 A | 11/1976 | Morrison | 250/312 |
| 5,099,846 A | 3/1992 | Hardy | 128/653.1 |
| 5,107,839 A | 4/1992 | Houdek et al. | 128/653.1 |
| 5,207,223 A | 5/1993 | Adler | 128/653.1 |
| 5,291,889 A | 3/1994 | Kenet et al. | 128/653.1 |
| 5,301,674 A | 4/1994 | Erikson et al. | 128/661.01 |
| 5,379,642 A | 1/1995 | Reckwerdt et al. | 73/625 |
| 5,391,139 A | 2/1995 | Edmundson | 600/7 |
| 5,411,026 A * | 5/1995 | Carol | 600/439 |
| 5,442,675 A | 8/1995 | Swerdloff et al. | 378/65 |
| 5,447,154 A | 9/1995 | Cinquin et al. | 128/653.1 |
| 5,483,961 A * | 1/1996 | Kelly et al. | 600/429 |
| 5,511,549 A | 4/1996 | Legg et al. | 128/653.1 |
| 5,531,227 A | 7/1996 | Schneider | 128/653.1 |
| 5,609,485 A | 3/1997 | Bergman et al. | 434/262 |
| 5,673,300 A | 9/1997 | Reckwerdt et al. | 378/65 |
| 5,690,108 A | 11/1997 | Chakeres | 128/653.1 |
| 5,715,166 A | 2/1998 | Besl et al. | 364/4.24 |
| 5,754,623 A | 5/1998 | Seki | 378/65 |
| 5,810,007 A | 9/1998 | Holupka et al. | |
| 5,851,183 A * | 12/1998 | Bucholz | 600/425 |
| 5,954,647 A * | 9/1999 | Bova et al. | 600/407 |
| 5,991,703 A | 11/1999 | Kase | 702/167 |
| 6,019,724 A * | 2/2000 | Gronningsaeter et al. | 600/439 |
| 6,106,470 A | 8/2000 | Geiser et al. | 600/443 |
| 6,117,081 A | 9/2000 | Jago et al. | 600/443 |
| 6,122,341 A | 9/2000 | Butler et al. | 378/20 |
| 6,129,670 A | 10/2000 | Burdette et al. | 600/427 |
| 6,208,883 B1 * | 3/2001 | Holupka et al. | 600/407 |
| 6,259,943 B1 * | 7/2001 | Cosman et al. | 600/429 |
| 6,285,805 B1 | 9/2001 | Gueziec | 382/299 |
| 6,292,578 B1 | 9/2001 | Kalvin | 382/131 |
| 6,345,114 B1 | 2/2002 | Mackie et al. | 382/132 |
| 6,359,959 B1 | 3/2002 | Butler et al. | 378/20 |
| 6,385,286 B1 | 5/2002 | Fitchard et al. | 378/65 |
| 6,390,982 B1 | 5/2002 | Bova et al. | 600/443 |
| 6,438,202 B1 | 8/2002 | Olivera et al. | 378/65 |
| 6,516,046 B1 | 2/2003 | Frohlich et al. | 378/65 |
| 6,535,574 B1 | 3/2003 | Collins et al. | 378/65 |
| 6,546,073 B1 | 4/2003 | Lee | 378/65 |
| 6,546,279 B1 * | 4/2003 | Bova et al. | 600/429 |
| 6,553,152 B1 | 4/2003 | Miller et al. | 382/294 |
| 6,560,311 B1 | 5/2003 | Shepard et al. | 378/65 |
| 6,591,127 B1 | 7/2003 | McKinnon | 600/411 |
| 6,628,983 B1 | 9/2003 | Gagnon | 600/431 |
| 6,636,622 B2 | 10/2003 | Mackie et al. | 382/132 |
| 6,641,539 B2 * | 11/2003 | Hirooka et al. | 600/459 |
| 6,661,870 B2 | 12/2003 | Kapatoes et al. | 378/65 |
| 6,683,985 B1 | 1/2004 | Kase et al. | 382/203 |
| 6,728,424 B1 * | 4/2004 | Zhu et al. | 382/294 |
| 2001/0035871 A1 | 11/2001 | Bieger et al. | 345/630 |
| 2002/0018588 A1 | 2/2002 | Kusch | 382/131 |
| 2002/0082494 A1 | 6/2002 | Balloni et al. | 600/410 |
| 2002/0156375 A1 | 10/2002 | Kessman et al. | 600/439 |
| 2002/0176541 A1 | 11/2002 | Schubert et al. | 378/205 |
| 2002/0183610 A1 | 12/2002 | Foley et al. | 600/407 |
| 2002/0188194 A1 | 12/2002 | Cosman | 600/426 |
| 2003/0018232 A1 | 1/2003 | Elliott et al. | 600/1 |
| 2003/0112922 A1 | 6/2003 | Burdette et al. | 378/65 |

FOREIGN PATENT DOCUMENTS

| | | |
|---|---|---|
| WO | WO 99/26534 | 6/1999 |
| WO | WO 99/27839 A2 | 6/1999 |
| WO | WO 99/27839 A3 | 6/1999 |
| WO | 03/076003 A2 | 9/2003 |
| WO | 03/076003 A3 | 9/2003 |

OTHER PUBLICATIONS

Booth, *Modelling the impact of treatment uncertainties in radiotherapy*, University of Adelaide, Mar. 2002), Section 2.4 (http://thesis.library.adelaide.edu.au/uploads/approved/adt-SUA20020816.175301/public/03chapter2.pdf.

Brujic et al., *Analysis of Free-Form Surface Registration*, International Conference on Image Processing, pp. 393-396 (1996).

Cuisenaire, O., http://www.tele.ucl.ac.be/PEOPLE/OC/these/node74.html, Posted Oct. 5, 1999, Downloaded from the Internet on Aug. 10, 2004.

Cuisenaire, O., http://www.tele.ucl.ac.be/PEOPLE/OC/these/node75.html, Posted Oct. 5, 1999, Downloaded from the Internet on Aug. 10, 2004.

Cuisenaire, O., http://www.tele.ucl.ac.be/PEOPLE/OC/these/node12.html, Posted Oct. 5, 1999, Downloaded from the Internet on Aug. 10, 2004.

Dubois et al. *Intraobserver and Interobserver Variability of MR Imaging- and CT-derived Prostate Volumes after Transperineal Interstitial Permanent Brachytherapy*, Radiology. 207(3):785-9 (1998).

Eggert et al., *Simultaneous Registration of Multiple Range Views for Reverse Engineering*, International Conference of Pattern Recognition, pp. 243-247 (1996).

Hanks, et al., *Three Dimensional Conformal External Beam Treatment Of Prostate Cancer* http://prostate-help.org/download/pilgrim/10rad.pdf.

Hanks et al., *Clinical and Biochemical Evidence of Control of Prostate Cancer at 5 Years After External Beam Radiation*, The Journal of Urology, vol. 154, 456-459 (1995).

Haralick et al., *Pose Estimation From Corresponding Data Point*, IEEE Transactions on Systems, Man, and Cybernetics, 19(6):1426-1446 (1989).

Hua et al., *Development of a Semi-Automatic Alignment Tool For Accelerated Localization of the Prostate*, Int. J. Radiation Oncology Biol. Phys., 55(3):811-823 (2003).

Jiang et al., *A New Approach to 3-d Registration of Multimodality Medical Images by Surface Matching*, SPIE vol. 1808 Visualization in Biomedical Computing, pp. 196-213 (1992).

Krempien et al., *Daily patient set-up control in radiation therapy by coded light projection*, 3 pages.

Michalski et al., *Three-Dimensional Conformal Radiation Therapy (3DCRT) for Prostate Cancer*, Radiation Oncology Center, Mallinckrodt Institute of Radiology, Washington University Medical Center, St. Louis, Missouri (1996) http://www.phoenix5.org/Infolink/Michalski/#3.

Paskalev et al., *Daily Target Localization for Prostate Patients based on 3-D Image Correlation*, Phys. Med. Biol., vol. 49, pp. 931-939 (2004).

Pennec et al,. *A Framework for Uncertainty and Validation of 3-D Registration Methods Based on Points and Frames*, International Journal of Computer Vision 25(3), 203-229 (1997).

Pito, *A Registration Aid*, International Conference on Recent Advanced in 3D Digital Imaging and Modelling, pp. 85-92 (1997).

Pollack et al., *Conventional vs. Conformal Radiotherapy for Prostate Cancer: Preliminary Results of Dosimetry and Acute Toxicity*, Int. J. Radiation Oncology Biol. Phys., 34(3):555-564.

Robb, *Three-Dimensional Visualization in Medicine and Biology*, Book Chapter in: Handbook of Medical Imaging: Processing and Analysis, ed. Isaac N. Bankman, Academic Press, San Diego, CA, Chapter 42, pp. 685-671 (2000).

Robinson, *Advances in Multi-Modal Data Analysis: The Analyze Software Environment*, http://www.ii.metu.edu.tr/~med-ii/makaleler/analyze_sw_enve.pdf, 5 pages. Downloaded on Aug. 10, 2004.

Soffen E.M. et al. *Conformal static field radiation therapy treatment of early prostate cancer versus non-conformal techniques: A reduction in acute morbidity*. Int J Radiat Oncol Biol Phys, 24: 485-488 (1992).

Thayananthan, A. et al., http://mi.eng.cam.ac.uk/~bdrs2/papers/thayananthan_cvpr03.pdf, pp. 1-8. Downloaded from the Internet on Aug. 10, 2004.

Tome et al., *Commissioning and Quality Assurance of an Optically Guided Three-dimensional Ultrasound Target Localization System for Radiotherapy*, Med. Phys., 29(8):1781-1788 (2002).

Zhang, *Iterative Point Matching for Registration of Free-Form Curves and Surfaces*, International Journal of Computer Vision, 13(2):119-152 (1994).

http://www.ucsf.edu/jpouliot/Course/chapter5.htm.

http://www.acmp.org/meetings/hershey_2001/highlights/benedict.pdf.

http://www.ucsf.edu/jpouliot/Course/Lesson22.htm.

http://www.gemedicalsystems.com/patient/see_treat/positioning.html.

http://www.emoryradiationoncology.org/high-technology.htm.

http://www.varian.com/pinf/imr000c.html.

http://www.ucsf.edu/jpouliot/Course/conformal_radiation_therapy.htm.

* cited by examiner

METHOD AND APPARATUS FOR LESION LOCALIZATION, DEFINITION AND VERIFICATION

BACKGROUND OF THE INVENTION

1. Field of the Invention

The invention relates to a method wherein the shape, form, position and configuration of a lesion or tumour, to be treated by a radiation therapy device, may be ascertained with greater definition, in order to better design a treatment plan for its eradication. In accordance with a further aspect, the invention also relates to method and apparatus for verification of the position of the lesion with respect to the radiation beam or beams prior to the execution of a radiation treatment. The invention relates to a method wherein the size, location and disposition of a tumour may be determined, updated and tracked prior to and during treatment therefor.

2. Description of Prior Art

The goal of modem day radiation therapy of cancerous tumours or lesions, is to eradicate the tumour while avoiding to the maximum extent possible damage to healthy tissue and organs in the vicinity of the tumour. Since the large majority of tumours are radioresponsive, they can be controlled or eradicated completely if a sufficient radiation dose is delivered to the tumour volume. However, the delivery of the necessary tumourcidal dose may result in certain complications due to damage of healthy tissue that surround the tumour, or due to damage to other healthy body organs located in the proximity of the tumour. Conformal therapy is a radiation treatment approach which attempts to combine accurate target localization with focused radiation delivery in order to conform the high dose region closely to the region defined by the outer surface of the tumour while minimizing the dose to surrounding healthy tissue or adjacent healthy organs. Various conformal therapy techniques are well known in the art.

Conformal radiation therapy employs dedicated radiation units capable of producing highly energetic radiation beams of photons, electrons or other charged particles. The radiation unit typically has a radiation source, which is typically mounted on a rotatable gantry of the radiation treatment unit. Through gantry rotation, the radiation source is rotated about the patient who is typically placed on a treatment table and the radiation beam is directed towards the tumour or lesion to be treated. Various types of devices are used to conform the shape of the radiation treatment beam to encompass tightly the outline of the tumour as seen by the radiation treatment beam as it traverses the patient's body into the tumour. An example of such a device is a multileaf collimator, which consists of a set of computer-controlled movable leaves or fingers, which can be positioned individually in and out of the radiation beam in order to shape it to the tumour outline. Various types of radiation treatment planning systems can create a radiation treatment plan which, once implemented will deliver a specified dose to the tumour while sparing the surrounding healthy tissue or adjacent healthy organs.

The basic problem in conformal radiation therapy is knowing the location of the target, or lesion or tumour, or alternatively of the healthy organs with respect to the intended placement of the radiation beam or field (I) prior to the design of a radiation treatment plan and (II) at the time of the radiation treatment. Localization of the target volume within the patient prior to the design of a radiation treatment plan is performed by acquiring a three-dimensional image of the patient with a conventional diagnostic imaging device such as computerized tomographic ("CT") imaging device, a magnetic resonance imaging ("MRI") device or a positron emission tomographic ("PET") imaging device, as they are known in the art. These sophisticated devices may be available from a variety of manufacturers, such as GE Medical Systems, Marconi, Toshiba, Siemens, Phillips and others.

At the present time, when the treatment is initiated, both the patient's position and the position of the target within the patient at the time of the radiation treatment are assumed to be grossly the same at as they were at the time the treatment plan was created. However, if the position of the target volume is not correctly determined (I) prior to the treatment plan creation or (II) at the time of treatment, treatment failures can occur in a sense that the conformal dose of radiation may not be delivered to the correct location within the patient's body. Failures of type (I) can occur if the conventional imaging modality fails to reveal completely the shape, location and orientation of the tumour or lesion or organ of interest. This may occur since not all conventional diagnostic imaging devices adequately, completely or fully determine the exact shape, size and orientation of a tumour, resulting in that even with the use of the most up-to-date diagnostic imaging device, some tumours may not be fully diagnosed. Failures of type (II) can occur as a result of organ displacement (motion) from day to day, which may occur from a variety of factors, such as growth of the tumour, change in the patient physionomy due to weight loss, or even patient breathing. Failures of type (II) can also occur from incorrect positioning of the patient on the treatment table of the radiation treatment unit.

To avoid the above failures, present day radiation treatment plans typically regard the target of the radiation to occupy a space in the patient's body, which is larger than it really is, in order to ensure that the smaller tumour or lesion, will fall within the larger volume. As a result, some healthy tissue or healthy organs surrounding the tumour or lesion will be irradiated with the maximum radiation dose intended for the tumour or target. Delivering the maximum radiation dose to a larger volume of healthy tissue or healthy organs may increase the risk of damaging these, and may for example, promote future cancers in the healthy surrounding tissue. For this reason oncologists using present conformal radiation therapy may decide to deliver a lower radiation dose to the intended treatment volume in order to spare the non-target tissue with the potential disadvantage of compromising the success of the treatment by underdosing some portion of the target organ.

In an attempt to improve the localization of the lesion for the treatment of prostate cancer and therefore rectify failures of type I, a method was disclosed Holupka et al., U.S. Pat. No. 5,810,007 which utilizes a transrectal probe to generate a two-dimensional ultrasound image. This image is then superimposed on an image acquired with a conventional diagnostic imaging device, such as CT scan. The image registration in the above said method requires the identification of at least 2 fiducials visible in both the ultrasound image and the image acquired with the conventional diagnostic imaging device. However, the following shortcomings may limit the utility of the above said method:

1. The transrectal ultrasound probe may considerably displace the lesion or organ thus providing inaccurate information about the spatial location of the lesion at treatment time if at that time the transrectal probe is not re-inserted. In any event, the insertion and removal of the probe prior to initiating treatment may cause displacement of the lesion, adding further uncertainty to the localization of the tumour. Moreover, inserting the transrectal probe for each treatment session can cause significant patient discomfort, resulting in this method not gaining popularity with physicians.

2. Holupka provides only for two dimensional images, and assumes that the 2D ultrasound image and the image obtained with the conventional diagnostic imaging modality are acquired in the same plane. For this case two identifiable fiducials in both images would be sufficient to register and superimpose the images. However, there is no certainty that the ultrasound image and the image from the conventional diagnostic imaging device are providing images in the same imaging planes and therefore a deviation of one image from the plane of another may considerably compromise the accuracy of the method.

3. The above said method registers and superimposes a two-dimensional ultrasound image onto a 2-dimensional image acquired with a conventional diagnostic imaging modality. Thus the ultrasound definition of the lesion is performed only in a single plane. For the purposes of three-dimensional conformal therapy, a two-dimensional definition of the lesion is incomplete and therefore inadequate since in other imaging planes, the extent of the lesion volume may be larger or smaller.

4. Further, Holupka is of limited application since it may only be used with respect to a very limited number of tumours, such as of the rectum, lower large intestine, and of the prostate. It can not be used for other type of tumours.

In attempt to rectify failures of type II, another system was proposed to verify the target or lesion position prior to a radiation treatment session by Carol, U.S. Pat. No. 5,411,026. The system comprises an ultrasound imaging device to acquire at least one ultrasound image of the lesion in the patient's body and a device to indicate the position of the ultrasound image generating device or probe with respect to the radiation therapy device. The above said system verifies that the actual position of the lesion immediately before the treatment session conforms to the desired position of the lesion in the radiation treatment plan by comparing the outlines of the outer surface of the lesion as defined on the at least one ultrasound image to the outline of the outer surface of the lesion as defined on the at least one of the diagnostic images obtained by a computerized tomographic ("CT") or alternatively by magnetic resonance imaging ("MRI") device and used for the design of the radiation treatment plan. However, the following shortcomings may limit the utility of the above said system.

1. The appearance of the tumour or lesion or organ in the ultrasound image or images can have an appearance different from that of tumour or lesion or organ in the images obtained with conventional diagnostic devices. Thus the process of comparing outlines of the outer surfaces of the tumour or lesion or organ as they appear in images obtained with different imaging devices may be inaccurate since these surfaces can be different both in appearance and extent. In other words, Carol compares apples and oranges, which results in an incomplete assessment of the tumour. Since the trend in conformal treatment is towards more accurate spatial delivery of the exact dose of radiation, this shortcoming is quite significant.

2. Carol also does not address failures of type I whereby the diagnostic images obtained with computed tomography or magnetic resonance imaging devices do not reveal completely the location or the extent of the tumour or lesion or organ, due to the inherent limitation of said devices with respect to certain tumours in certain locations. Furthermore if the computed tomography or magnetic resonance diagnostic images do not reveal, or completely reveal, the tumour or organ or lesion, Carol will lack the means to outline an outer surface to serve as a reference for the comparison to the outer surface of the tumour or lesion or organ outlined on the one or more ultrasound images.

In view of the above description of the prior art it is therefore an object of the invention to provide an improved method and apparatus for radiation therapy treatments to decrease the rate of occurrence of the above defined failures of type I and type II.

It is another object of the invention to provide a novel method and apparatus for accurate localization, sizing and definition of tumour or lesion or other organ volume in preparation for radiation therapy.

It is an object of the present invention to provide for the use of ultrasound imaging at the planning stage of a treatment plan;

It is a further object of the invention to provide an improved method and apparatus for establishing an ultrasound image or plurality of ultrasound images for target definition and localization and correlating this image or plurality of ultrasound images to radiation therapy simulator images, obtained with conventional diagnostic imaging devices such as a computerized tomographic ("CT") imaging device, a magnetic resonance imaging ("MRI") device or a positron emission imaging device ("PET"), or any other type, such as for example future types of diagnostic devices.

It is also an object of the present invention to provide a novel method for three-dimensional superposition of a three-dimensional ultrasound image of a lesion onto another three-dimensional lesion image, such as CT or MRI or another ultrasound image.

It is yet another object of the invention to provide an improved method and apparatus for accurate positioning of the target relative to radiation therapy beams based on the registration of an ultrasound image or plurality of ultrasound images acquired immediately before or after the acquisition of conventional diagnostic images to an ultrasound image or plurality of images acquired immediately before a radiation treatment session.

The invention relates to a method and apparatus for (a) lesion localization and tumour or lesion or organ definition for radiotherapy treatment planning and (b) for verification and rectification of lesion position during radiotherapy treatment.

SUMMARY OF THE INVENTION

In accordance with one aspect, the present invention may include a number of steps to improve the localization, sizing, definition and orientation of a tumour or lesion or organ or of any other area of a body. Although the present invention may be contemplated for cancer treatment in humans, it is understood that it may also be used for other, non cancer treating medical applications, in both humans and animals.

In accordance with a general aspect, the localization, sizing, etc. . . . of a tumour may be necessary in order to devise a treatment plan for the treatment or eradication a tumour, or for any other necessary or required medical investigation. The steps may comprise: disposing the patient on the table of the conventional diagnostic imaging device; acquiring a diagnostic image or plurality of diagnostic images, using any known conventional diagnostic imaging device, such as for example, a CT, MRI or PET scan. Said acquisition may comprise the use of a number of fiducials placed on the patient surface so that the geometric orientation of the diagnostic image or images can be determined with respect to the diagnostic imaging device; acquiring an ultrasound image or plurality of ultrasound images immediately before or immediately after the acquisition of the diagnostic images with the ultrasound image generating means being disposed in a known geometric orientation with respect to the diagnostic imaging device for each ultrasound image generated; superimposing (known in the art as fusing) or combining the ultrasound image or images with the diagnostic image or images with the previous knowledge about their geometric orientation: outlining the contours of the outer surface of the tumour or lesion or organ on the ultrasound image or images and simultaneously displaying the above, said outer surface on the diagnostic image or images; employing the above said contours of the outer surface of the tumour or lesion or organ for the design of a radiation treatment plan.

With respect to the verification of the tumour or lesion or organ position with respect to the radiation therapy device the present invention may include the steps of: disposing the patient on the treatment table of a radiation therapy device; generating at least one ultrasound, i.e. US, image of the lesion in the patient's body with the US image generating means, that is the probe, being disposed in a known geometric orientation for each US image generated; comparing the above said ultrasound image or images to the ultrasound image or images obtained at the time of the acquisition of the diagnostic images whereby the position of the tumour or lesion or organ with respect to the radiation therapy device may be verified to establish conformity with the desired position of the tumour or lesion or organ in the radiation treatment plan.

Another feature of the present invention may include the method of comparing or registering the ultrasound image or images acquired immediately before the radiation treatment session to the ultrasound image or images obtained immediately before or after the acquisition of the diagnostic images. This method may employ either gray-level image correlation without the need of contour outlines or alternatively the registration of geometric objects (as known in the art) composed of the outlines the outer surface of the tumour or lesion or organ as defined on the ultrasound image or images acquired in the diagnostic and the radiation therapy room.

As a result of the above said image comparison another feature of the present invention is the step of determining the necessary tumour or lesion or organ displacement in order to dispose the tumour or lesion or organ in the desired position prescribed by the radiation treatment plan. A further feature of the present invention may include the step of performing the above determined tumour or lesion or organ displacement by but not restricted to, moving the treatment table with respect to the radiation treatment device, rotating the treatment table with respect to the radiation treatment device, rotating the collimator of the radiation treatment device as well as rotating the gantry of the radiation therapy device, or any combination of the above.

Therefore, in accordance with one aspect of the present invention, there is provided with:

a method for spatially localizing a tumour for the purposes of radiation treatment planning comprising the steps of:

generating one or more diagnostic images of said tumour using a diagnostic imaging device selected from the group comprising a CAT scan, PET scan, CT scan, assigning said tumour on said diagnostic image a first three-dimensional coordinate using an absolute coordinate reference system, generating one or more ultrasound image of said tumour using an ultrasound device assigning said tumour on said ultrasound image a second three-dimensional coordinate using said absolute coordinate reference system, fusing said ultrasound image and said image using said first and said second three-dimensional coordinates so as to obtain an accurate image of the tumour.

In accordance with a further embodiment, the present invention provides for:

a method for spatially localizing a tumour for the purposes of radiation treatment planning comprising the steps of:

placing on the patient a plurality of fiducials in proximity to the estimated position of said tumour, assigning a first three-dimensional coordinate to said fiducials using an absolute coordinate system, generating one or more diagnostic images of said tumour using a diagnostic imaging device selected from the group comprising a CAT scan, PET scan, CT scan, said at least one diagnostic image comprising thereon an image of said tumour and further comprising said fiducials, assigning said tumour on said at least one diagnostic image a second three-dimensional coordinate using said first three-dimensional coordinate of said fiducials as a reference, generating one or more ultrasound image of said tumour using an ultrasound device, said at least one ultrasound image comprising thereon an image of said tumour and further comprising said fiducials, assigning said tumour on said ultrasound image a third three-dimensional coordinate using said first three-dimensional coordinate of said fiducials as a reference, fusing said ultrasound image and said image using said second and said third three-dimensional coordinates so as to obtain an accurate image of the tumour.

In accordance with yet a further aspect of the present invention, there may be provided for a method for spatially localizing a tumour for the purposes of radiation treatment planning comprising the steps of:

placing on the patient a plurality of fiducials in proximity to the estimated position of said tumour, assigning a first three-dimensional coordinate to said fiducials using an absolute coordinate system, generating one or more diagnostic images of said tumour using a diagnostic imaging device selected from the group comprising a CAT scan, PET scan, CT scan, said at least one diagnostic image comprising thereon an image of said tumour and further comprising said fiducials, assigning said tumour on said at least one diagnostic image a second three-dimensional coordinate using said first three-dimensional coordinate of said fiducials as a reference, generating one or more ultrasound image of said tumour using an ultrasound device, said at least one ultrasound image comprising thereon an image of said tumour, using a positioning system configured so as to allow the position and orientation of said one or more ultrasound image to be known, such that a tumour on said one or more ultrasound image may be assigned a third three-dimensional coordinate in said absolute coordinate reference system, fusing said ultrasound image and said image using said second and said third three-dimensional coordinates so as to obtain an accurate image of the tumour.

In accordance with another aspect of the present invention, there is provided for:

a system for spatially localizing a tumour for the purposes of radiation treatment planning comprising:

a diagnostic imaging device selected from the group comprising a CAT scan, PET scan, CT scan, said diagnostic imaging device being adapted for generating at least one diagnostic image of said tumour, an ultrasound device, said ultrasound device being adapted for generating at least one ultrasound image of said tumour, a means for providing an absolute coordinate reference system, such that said tumour is assigned with a first three-dimensional coordinate on said diagnostic image, and a second three-dimensional coordinates on said ultrasound image a means for fusing said diagnostic image and said ultrasound image using said first three-dimensional coordinate and said second three-dimensional coordinate so as to obtain an accurate image of said tumour.

DETAILED DESCRIPTION OF THE INVENTION

An illustration of an embodiment of the method and apparatus of the present invention is shown in the components of the apparatus and images derived from the figures. In the schematic diagram of FIG. 1 the embodiment of the invention is generally illustrated. In order to achieve one of the objectives of the present invention, that is, to obtain the most accurate possible definition of the size, location and orientation of a tumour 010, it has been found that the target area of a patient's body 009 believed to comprise a tumour 010 may be scanned or diagnosed using two distinct diagnostic apparatuses, and that the resulting images be compared. This may be achieved by comparing the image of the tumour 010 acquired through the use of a diagnostic device selected from group comprising an MRI, CT or PET with the image of the tumour 010 obtained with an ultrasound apparatus, such as those of Acuson, GE Medical Systems, Siemens, Toshiba and others. The order in which the two images is acquired is generally of no consequence, as long as the images are acquired within a short period of time of the other, for example, but not limited, to within one hour.

Figure 2:
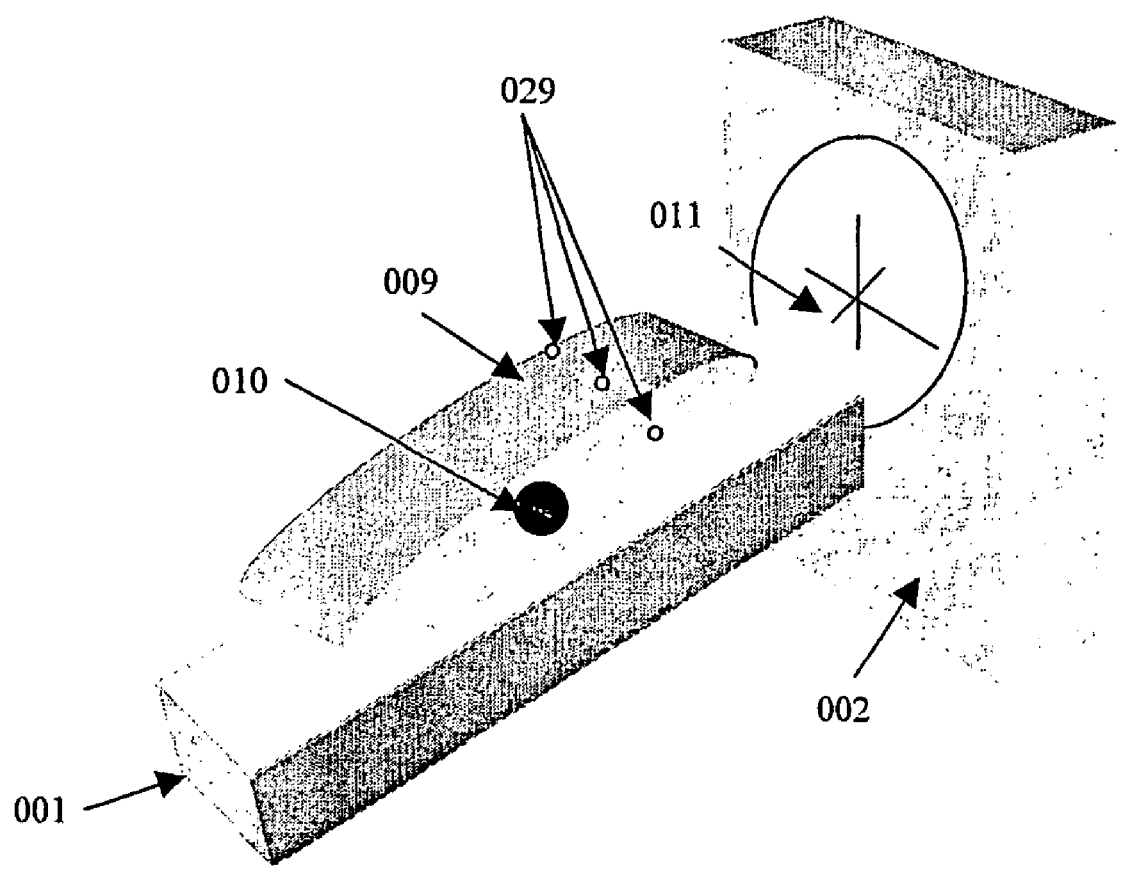
FIG. 2 is a perspective view of a conventional diagnostic imaging device with a patient schematically illustrated on the imaging table.
Figure 3:
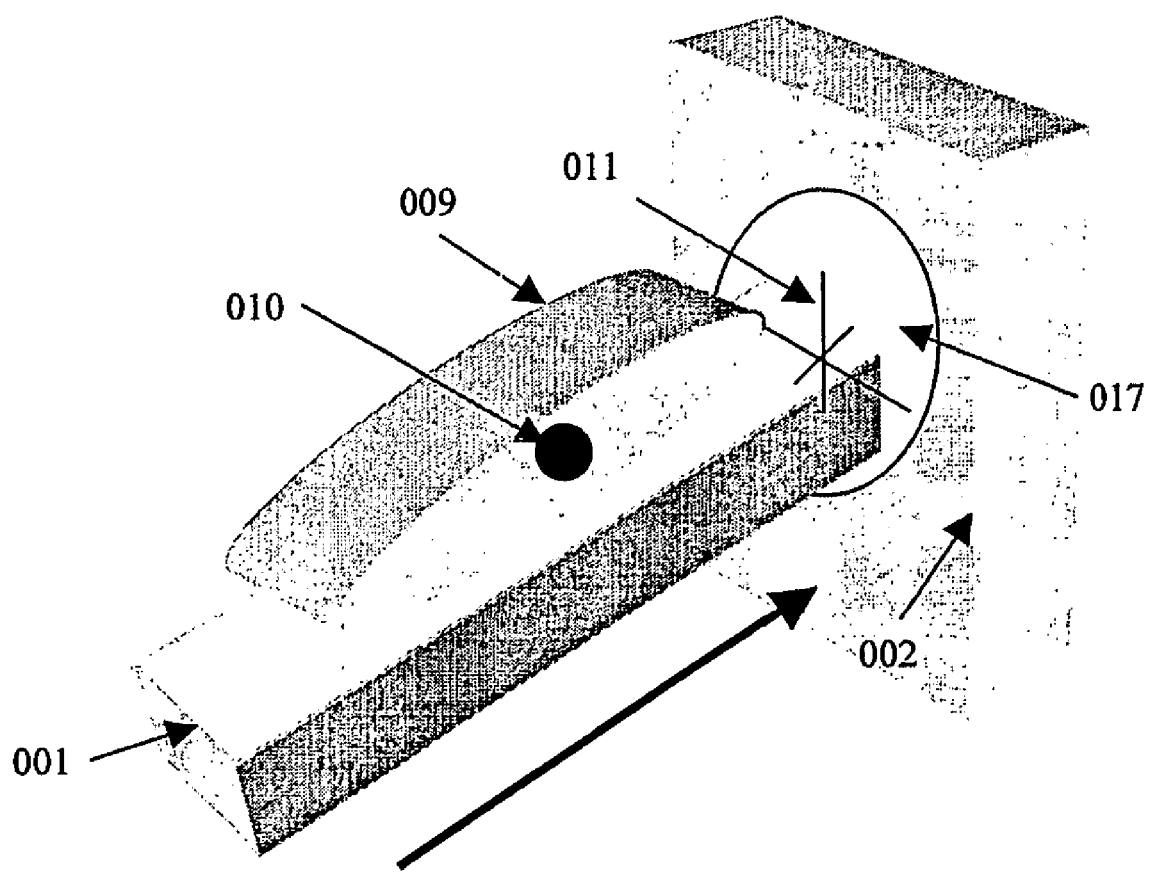
FIG. 3 is a further perspective view of an imaging device of FIG. 2.
Figure 6:
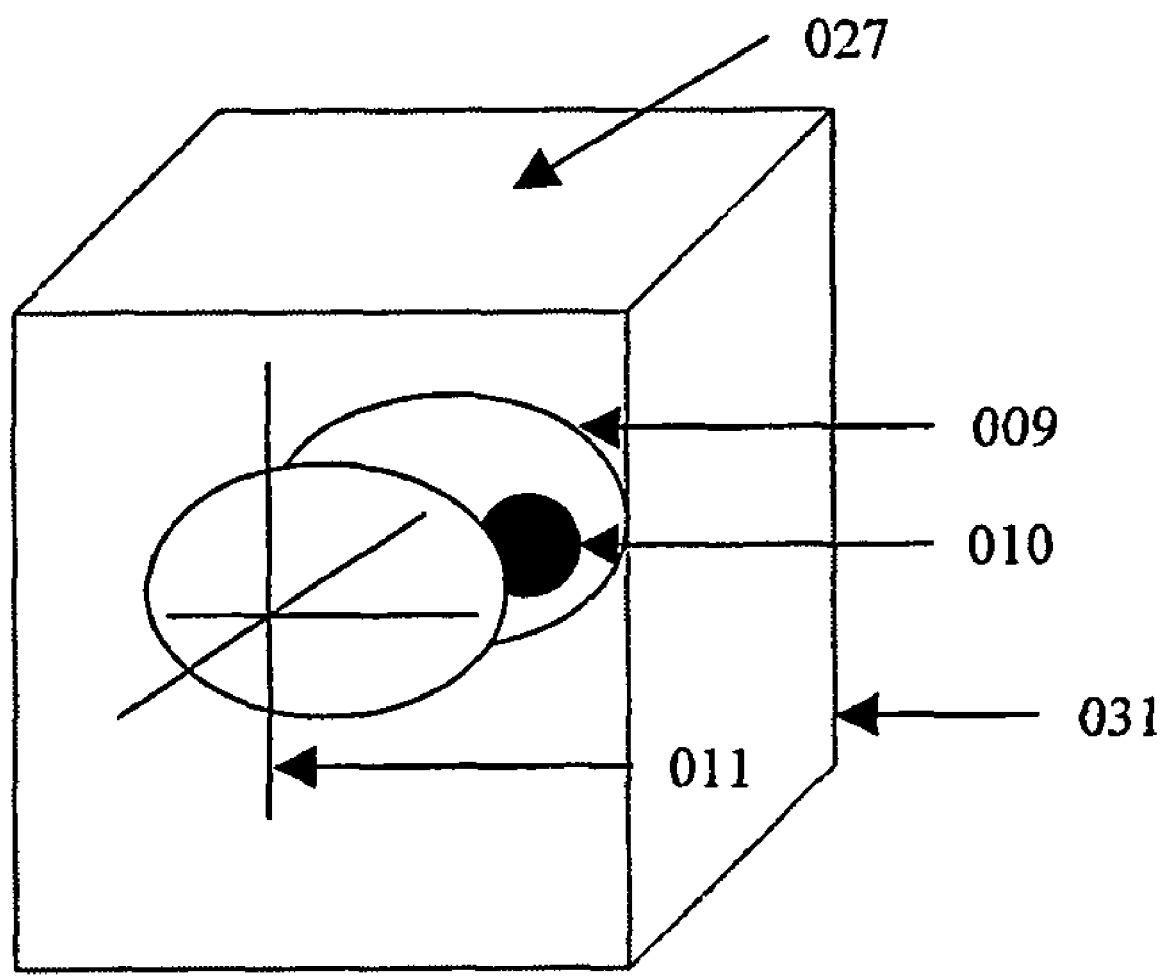
FIG. 6 is a representation of the three-dimensional diagnostic image data reconstructed from the multiple diagnostic images such as the one depicted in FIG. 5.

In accordance with this aspect, the first image to be acquired may for example, be acquired through the use of a diagnostic imaging device 002, which may be, for example, a computerized tomography ("CT") scanner, a magnetic resonance imaging ("MRI") scanner or alternatively a positron emission tomography ("PET") scanner, or any other equivalent device, or any other image producing diagnostic device. With reference to FIG. 2, a (conventional) diagnostic imaging device 002 is schematically shown with a conventional imaging table 001, upon which a patient 009 having a tumour or a lesion or an organ of interest 010 may be disposed. The diagnostic imaging device 002 may produce a cross-sectional image 023 or a "slice" of the body tissue, one such "slice" being schematically illustrated in FIG. 4, with the tumour or lesion or organ of interest 010 shown. Several diagnostic images 023 may be acquired by causing relative motion between the diagnostic imaging device 002 and the patient 009 in the slice acquisition space 017 of the diagnostic imaging device 002 as shown, for example, in FIG. 3. FIG. 6 illustrates a three-dimensional picture 027 formed or reconstructed from a plurality of (consecutive) diagnostic images 023 of parts or sections of the patient 009.

Figure 1:
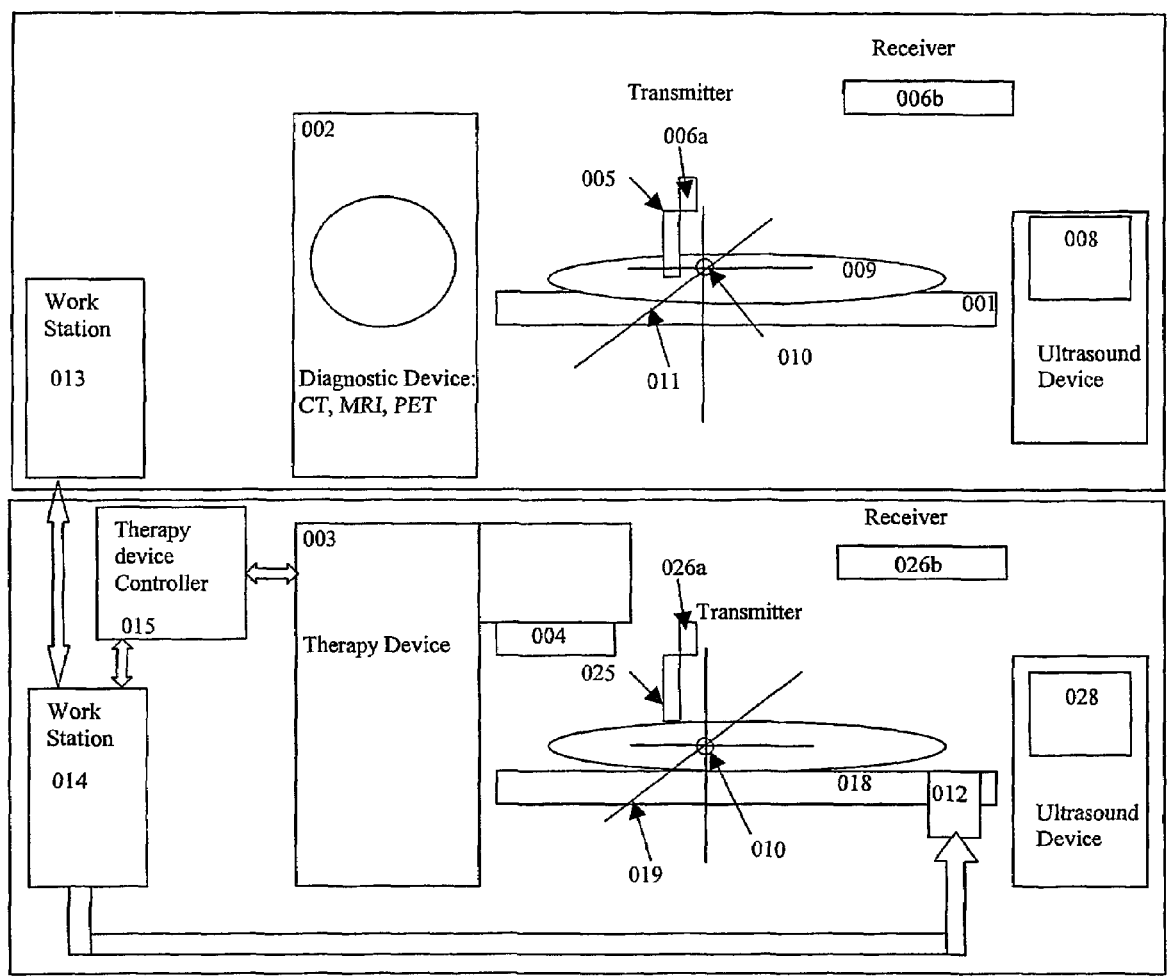
FIG. 1 is a functional block diagram of an embodiment of the present invention.

Since the image of the tumour 010 as acquired with the diagnostic imaging device 002 is to be compared with the image of the same tumour 010 taken with an ultrasound device 005, 008 as seen in FIG. 1, it is necessary for the tumour to be referenced, i.e., given a set of coordinates which will allow said comparison to be effective. For example, said coordinates may be independent of both the diagnostic imaging device 002 and of the ultrasound device 005, 008. However, the coordinate system may have to be able to correlate the position of a tumour 010 found with the diagnostic imaging device 002 with the position of the same tumour 010 found with the ultrasound imaging device 005, 008. Therefore an absolute coordinate system 011 may need to be established.

Figure 5:
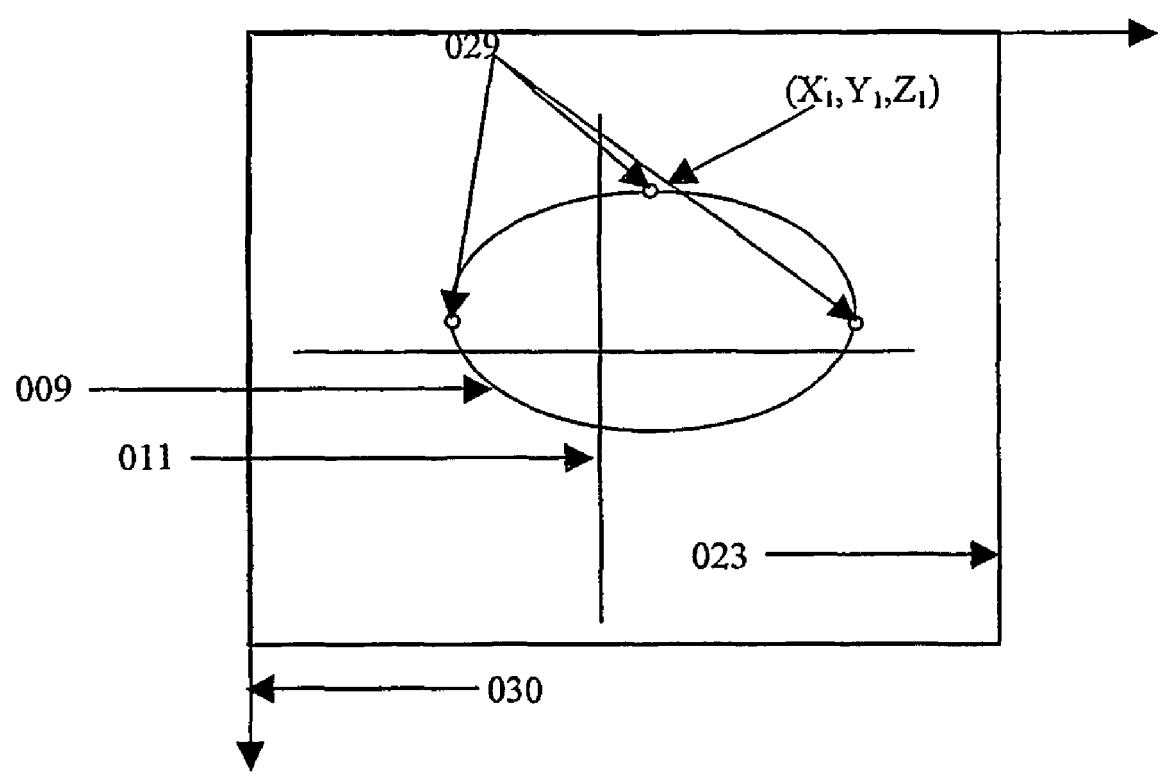
FIG. 5 is an example of an image produced by the imaging device of FIG. 2 illustrating fiducials with known positions with respect to the diagnostic imaging device and visible on the diagnostic image or images.

To that end, a means for assigning an absolute coordinate to the tumour 010 on an absolute coordinate system 011 may be provided, which absolute coordinate may be used to correlate the, for example CT image of the tumour 010 with the ultrasound image thereof. In order to do so, a number of markers, also known as fiducials, for example, three fiducials 029 as illustrated in FIG. 5, may be placed on the patient's body 009 in or around the vicinity of the lesion before the acquisition of the diagnostic images 023. In accordance with one practice, the fiducials 029 may all be placed in the same plane. The position of the fiducials (which may be any physical markers which may be easily seen or identified in a diagnostic image) may then be ascertained in the absolute coordinate system 011 through the use of any known system, for example a measurement system.

The measurement system may take any known shape or form. For example, the measurement system may, in one embodiment, comprise one or more lasers, or laser systems, which lasers may for example be disposed on the walls or the ceiling of the room in which the diagnostic imaging device 002 is located. Such measurement systems are known in the art, and may for example, be purchased commercially from a company called Cemar Electric, product Cermaligne, model number CL 505-CH2. The lasers, or any other suitable device, may be directed at the fiducials, and through the laser beams being bounced back off of the fiducials to their source or to any other measurement device, the coordinates of the fiducials may be determined and assigned. As a result, the fiducials may be assigned absolute coordinates, for example, $X_1$, $Y_1$, $Z_1$, as illustrated in FIG. 5. The measurement system may then download or forward said absolute coordinates of the fiducials to the diagnostic imaging device.

From the slice 023 illustrated in FIG. 5, which shows both the fiducials 029 and the tumour 010 on the same slice, it may then be possible to assign an absolute coordinates in the absolute coordinate system 011, to any point of the tumour 010. This may be done through a simple correlation based on the relative position of the fiducials 029 and tumour 010 as depicted in image slice 023 and measured in the image coordinate system 030 of slice 023. Since the coordinates of the fiducials 029 are known in the absolute coordinate system 011 and the relative position of the tumour 010 is known with respect to the fiducials 029 from information shown in slice 023 of FIG. 5, a conventional fitting algorithm known to those of ordinary skill in the art can be used to determine a transformation matrix, or coordinate transformation so as to assign absolute coordinates to any point in the tumour 010, for example $X_2, Y_2, Z_2$. The determination of the coordinates (X, Y, Z) of any object within diagnostic image 023 or 027 may be accomplished in this manner, and therefore assigned absolute coordinates within the absolute coordinate system 011.

Figure 4:
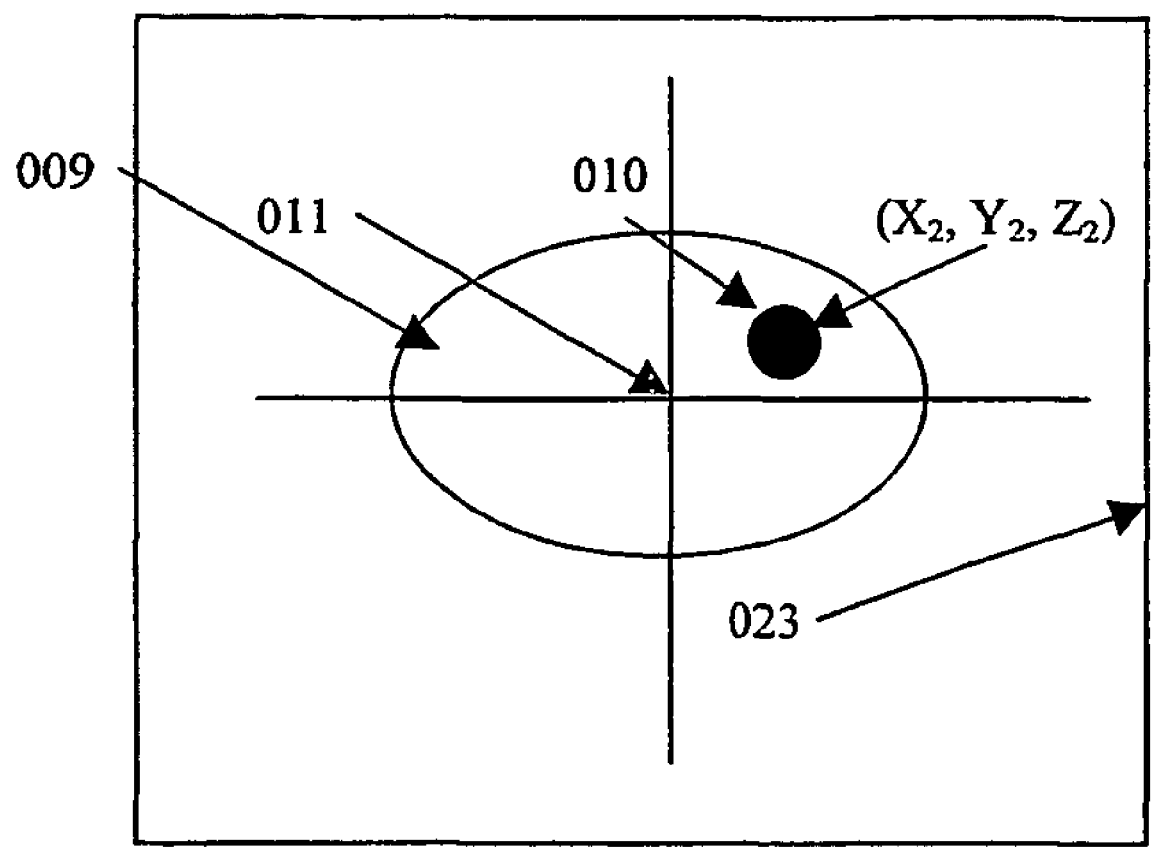
FIG. 4 is an example of an image produced by the imaging device of FIG. 2 illustrating the position of the lesion within the patient body.

Although FIGS. 4 and 5 are shown as having the absolute coordinate system 011 disposed through the patient 009, it is understood that said absolute coordinate system 011 may be disposed otherwise than through the body 009.

Figure 7:
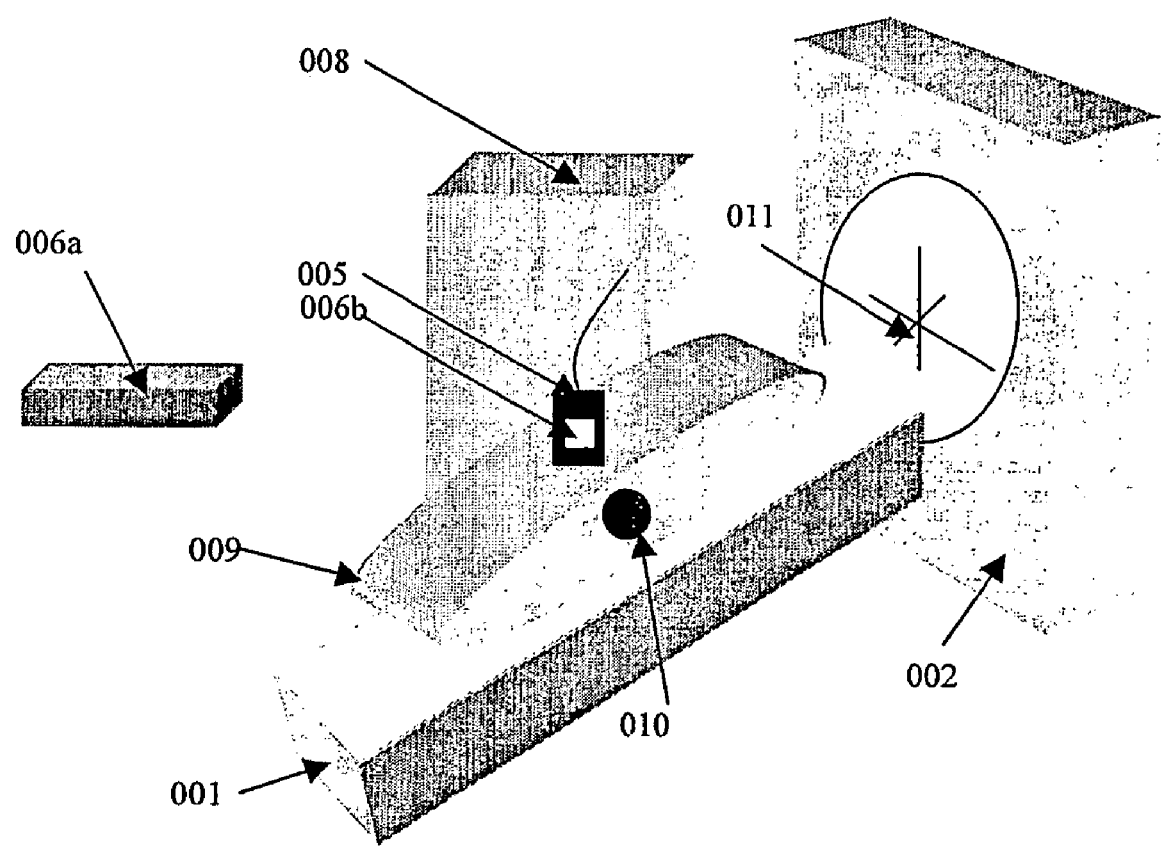
FIG. 7 is a perspective schematic view of the conventional diagnostic imaging device of FIG. 2, including a means for generating an ultrasound image of the lesion with the patient's body.
Figure 8:
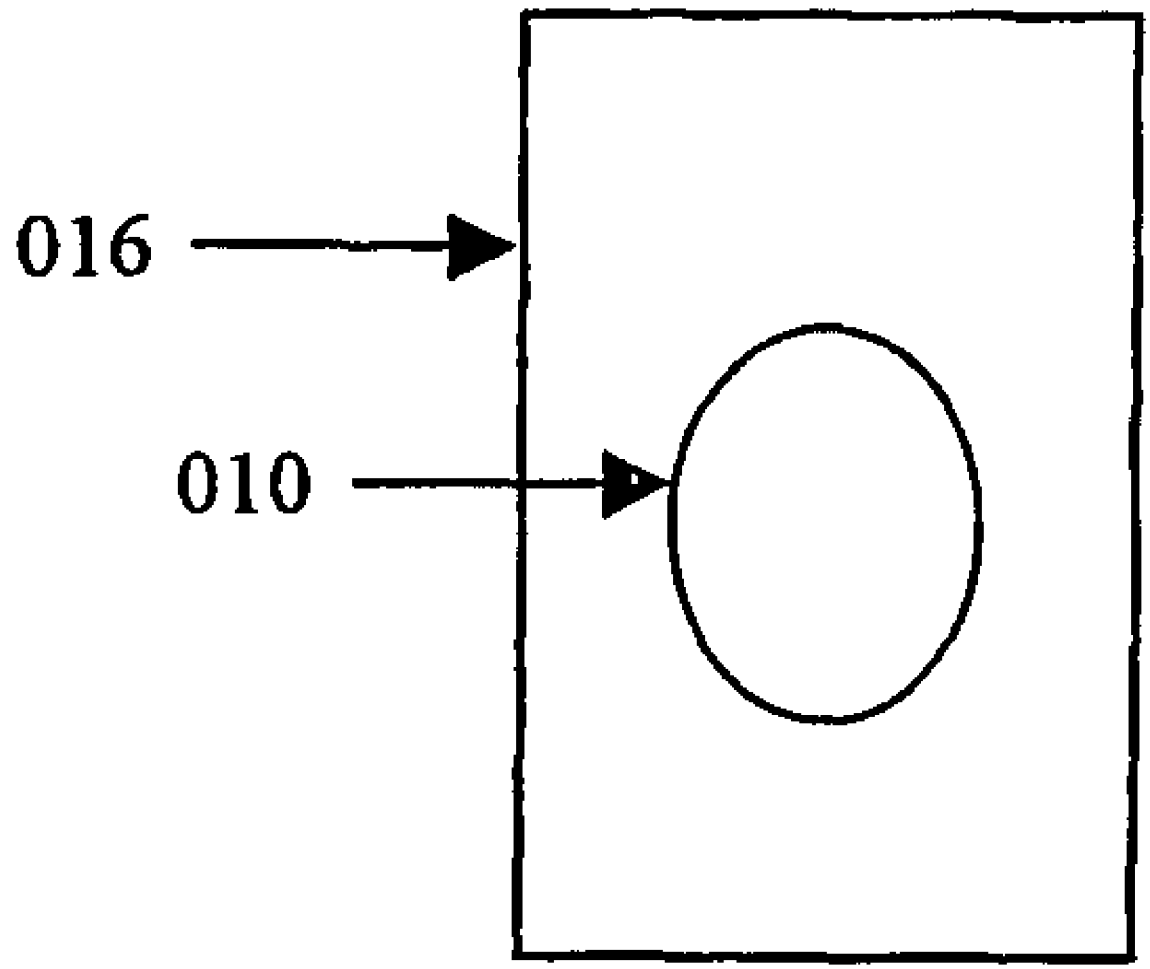
FIG. 8 is a representation of an ultrasound image of the tumour or lesion or organ.
Figure 9:
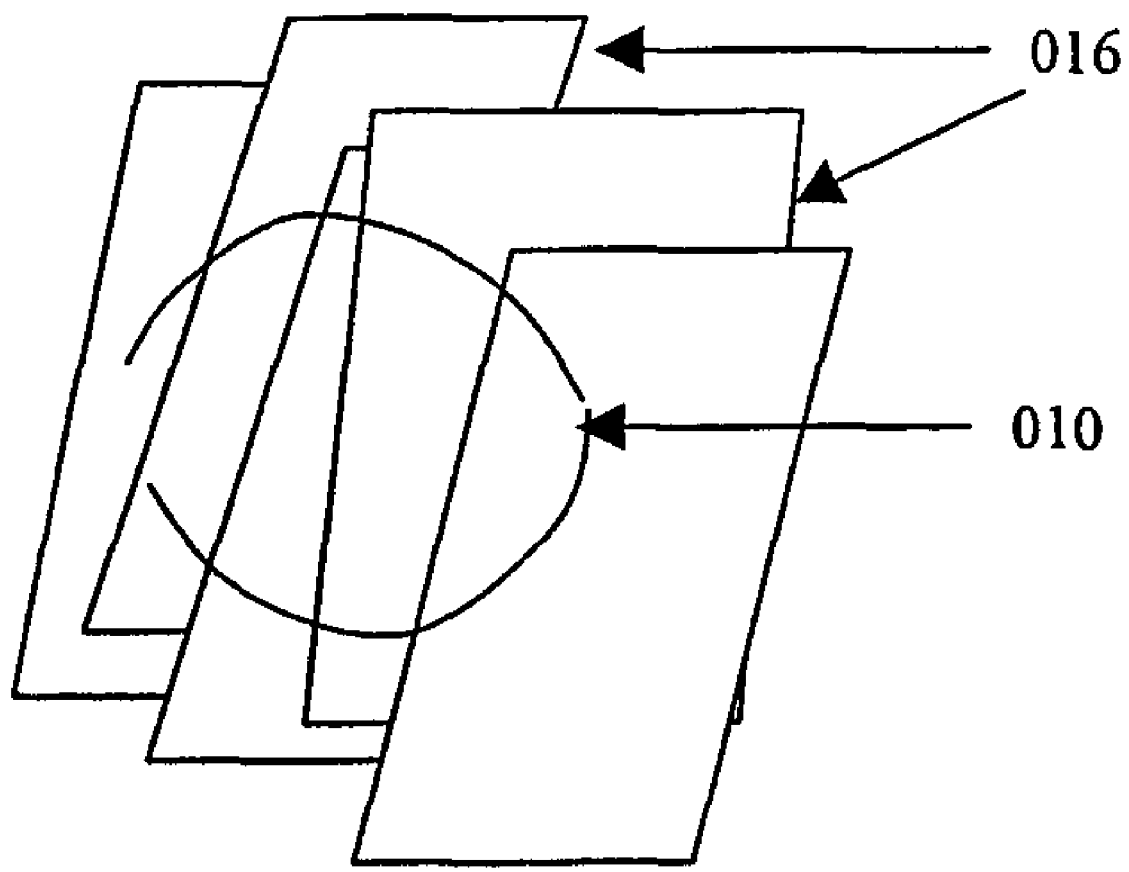
FIG. 9 is a perspective view indicating multiple ultrasound images being taken of a lesion with the ultrasound apparatus of FIG. 7

An additional step in the determination of the size, location and orientation of a tumour 010 may be illustrated in FIG. 7, wherein a means 005, 008 for generating at least one ultrasound image 016 of the lesion 010 is shown. Said means 008 for generating at least one ultrasound image may be disposed in the diagnostic imaging room where the diagnostic image device 002 is located. The means 008 for generating an ultrasound image 016 may utilize a conventional, commercially available ultrasound probe 005. The ultrasound probe 005 may be brought into contact with the patient's body 009 in order to generate the ultrasound image or images 016 of the tumour or lesion or organ 010, as illustrated in FIG. 8. As illustrated in FIG. 9, by moving, displacing or rotating the ultrasound probe 005, a plurality of ultrasound images 016 of the tumour or lesion or organ 010 may be acquired in various planes. In FIG. 9, the lesion 010 is shown disposed within the plurality of ultrasound images 016 with the plane of each ultrasound image representative of the orientation of the ultrasound probe 005 at the time of the ultrasound image acquisition. As may be seen, the planes may not necessarily be parallel to each other. From the plurality of the ultrasound images 016 a reconstruction of the three-dimensional volume or picture 031 (FIG. 10) of the ultrasound data may be performed.

In order to accurately reconstruct the three-dimensional volume 031 from the ultrasound data, and in order to assign an absolute coordinate in the absolute coordinate system 011, the orientation and the position (hereafter referred to as the orientation) of the ultrasound probe 005 with respect to the absolute coordinate system 011 must be known at the time each ultrasound of the tumour 010 is made. In order to accomplish this, a means 006a, 006b for indicating the (spatial) orientation of the ultrasound probe 005 may be used, and in particular may be disposed in the room of the diagnostic device 002 as shown in FIG. 7. Any conventional position sensing system may be used as means 006a, 006b to determine the position and the orientation of the ultrasound probe 005. For example, such systems are known in the art, sometimes generically called tracking systems, and may be available commercially from Ascension Technology Corporation, InterSense, Northern Digital Inc. Motion Analysis Corp. and others. The use of said position sensing means 006a and 006b may enable the determination of the position of said probe with respect to the absolute coordinate system 011. For example, the positioning systems may include, but is not limited to: a camera system fixed in the room which looks at light emitting or reflective markers mounted on the ultrasound probe 005; ultrasonic system with emitters mounted on the probe 005 with a detector measuring the distances to these emitters by time measurements and consequent geometric triangulation to determine the ultrasound probe 005 position and orientation; a positioning system based on a mechanical arm with the ultrasound probe 005 attached to the arm. It is to be noted that neither the ultrasound probe 005 nor the means 006a, 006b for indicating the geometric orientation of the ultrasound probe 995 have to be fixed to the table 001 of the diagnostic imaging device 002.

Figure 10:
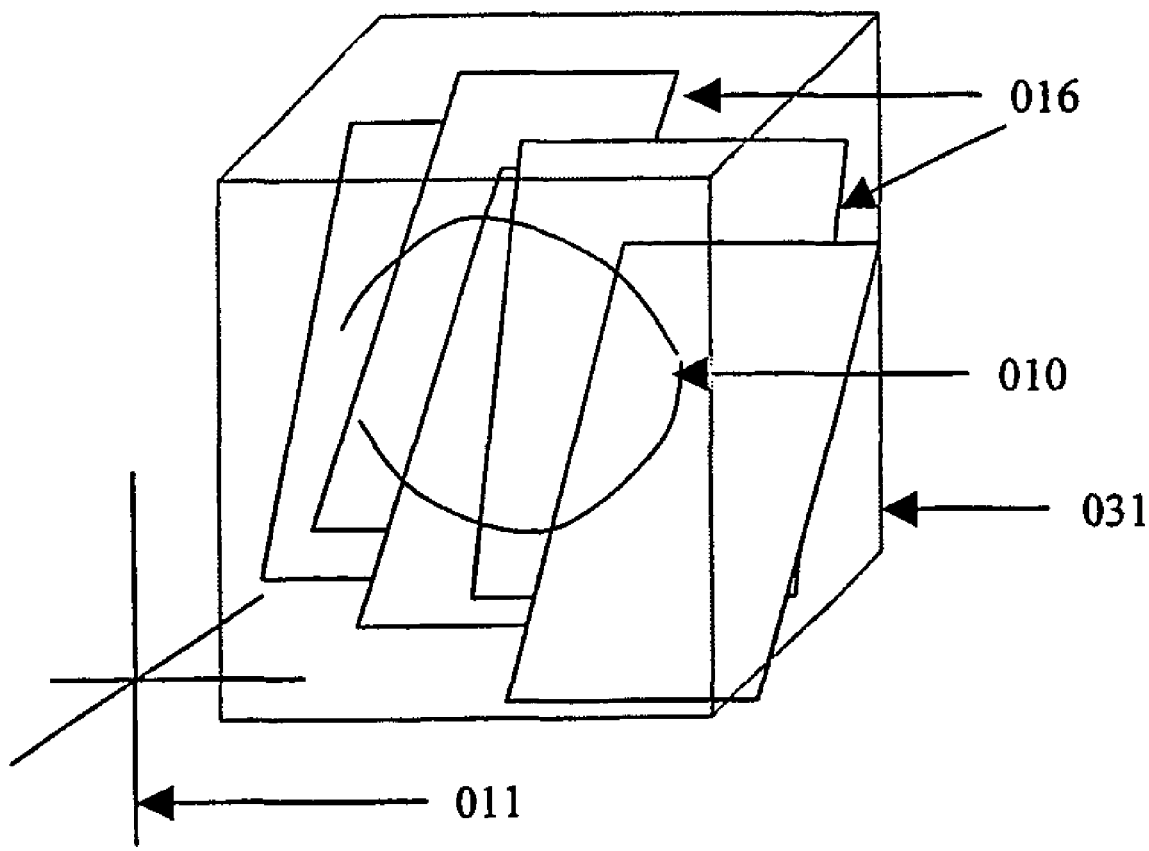
FIG. 10 is a representation of the three-dimensional ultrasound image data reconstructed from the multiple ultrasound images acquired in the room of the diagnostic imaging device and depicted in FIG. 9.

The means 006a, 006b for determining the coordinates and the geometric orientation of the ultrasound probe 005 are coordinated, aligned, connected or calibrated to the absolute coordinate system 011 i.e., for example, the lasers. As a result of this alignment or calibration, the coordinates (X, Y, Z) in the absolute coordinate reference system 011 of any point or feature in an ultrasound images 016 may be ascertained. In other words, the lasers which may form the basis of the absolute coordinate system 011, may be used to determine the absolute coordinates of a tumour 010 taken with an ultrasound image, as illustrated in FIG. 10.

Because the absolute coordinate system 011 is common to both the diagnostic imaging device 002 and the ultrasound device 005, it is possible to accurately correlate the position of a tumour 010 with respect to both systems. With this knowledge, the value of the ultrasound image data for each point within the reconstructed volume 031 (FIG. 10) can be determined by interpolating algorithms known to those of ordinary skill in the art. The acquisition control and fusion software may be executed on a dedicated computer or workstation 013 as illustrated in FIG. 1. Standard segmentation and other image enhancing tools are available to facilitate the process of lesion outlining and rendering.

Figure 11:
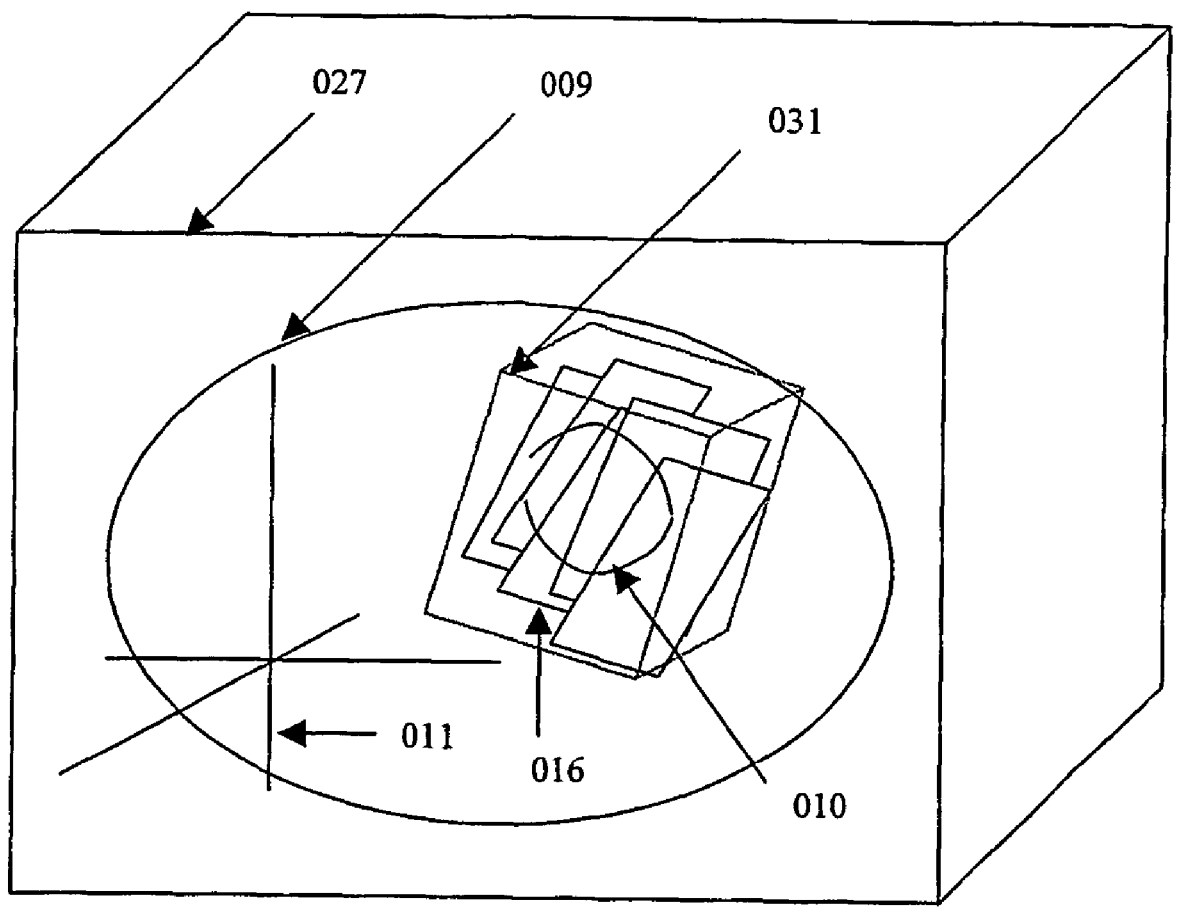
FIG. 11 is a representation of the three-dimensional ultrasound and diagnostic image data sets superimposed or combined.

Since the acquisition of the plurality of ultrasound images 016 is done before or immediately after (i.e. immediately before or immediately after) the acquisition of the plurality of diagnostic images 023, the ultrasound three-dimensional image data 031 and the diagnostic three-dimensional image 027 represent pictures of spatially overlapping volumes or sections of the patient anatomy at two very close moments of time. For a large number of anatomical sites it can be assumed that, within the accuracy required for treatment planning, the patient anatomy at these two very close moments of time does not change and therefore both the ultrasound three-dimensional image data 031 and the diagnostic three-dimensional image data 027 represent temporally identical, spatially overlapping sections of the same patient anatomy. Given that the positions and the orientations of both the ultrasound three-dimensional image data 031 and the diagnostic three-dimensional image data 027 are each known with respect the absolute coordinate reference system 011 of the diagnostic device 022 the ultrasound three-dimensional image data 031 and the diagnostic three-dimensional image data 027 can be superimposed, i.e. accurately superimposed as illustrated in FIG. 11.

Figure 12:
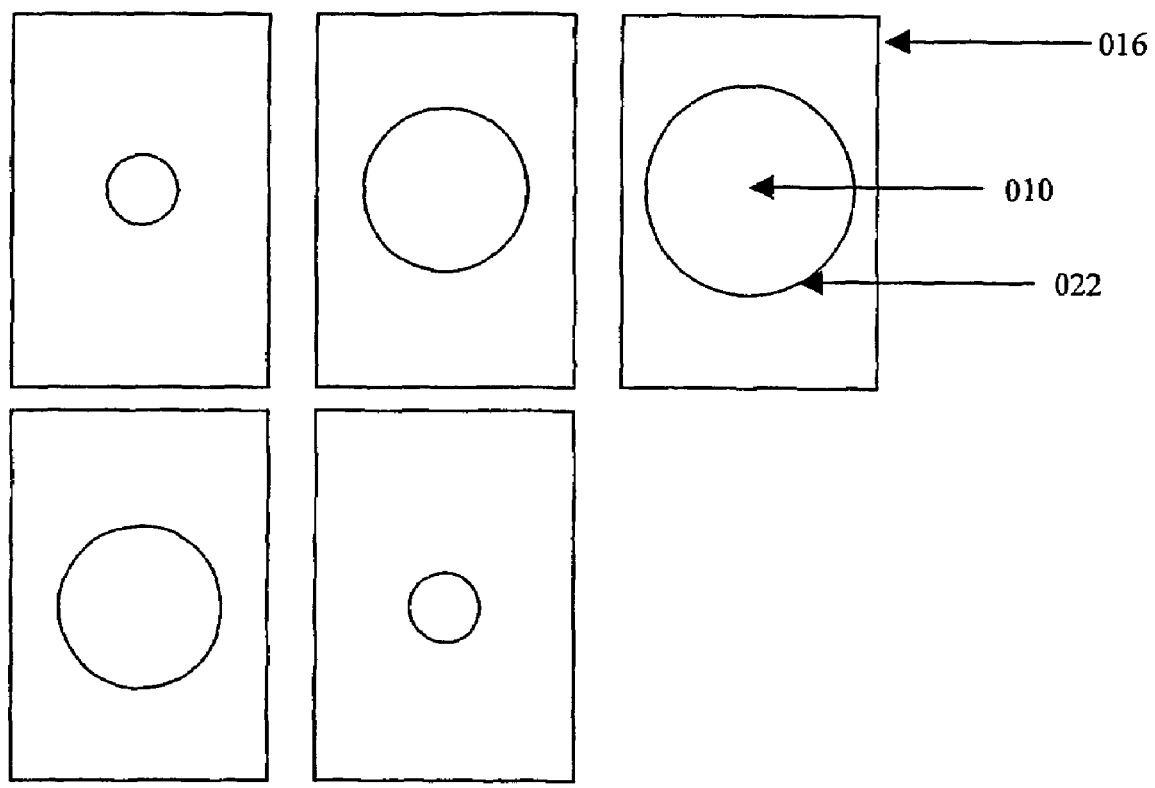
FIG. 12 is a representation of a sequence of two-dimensional ultrasound pictures of the lesion within the three-dimensional ultrasound data with the lesion having its outer surface outlined.
Figure 13:
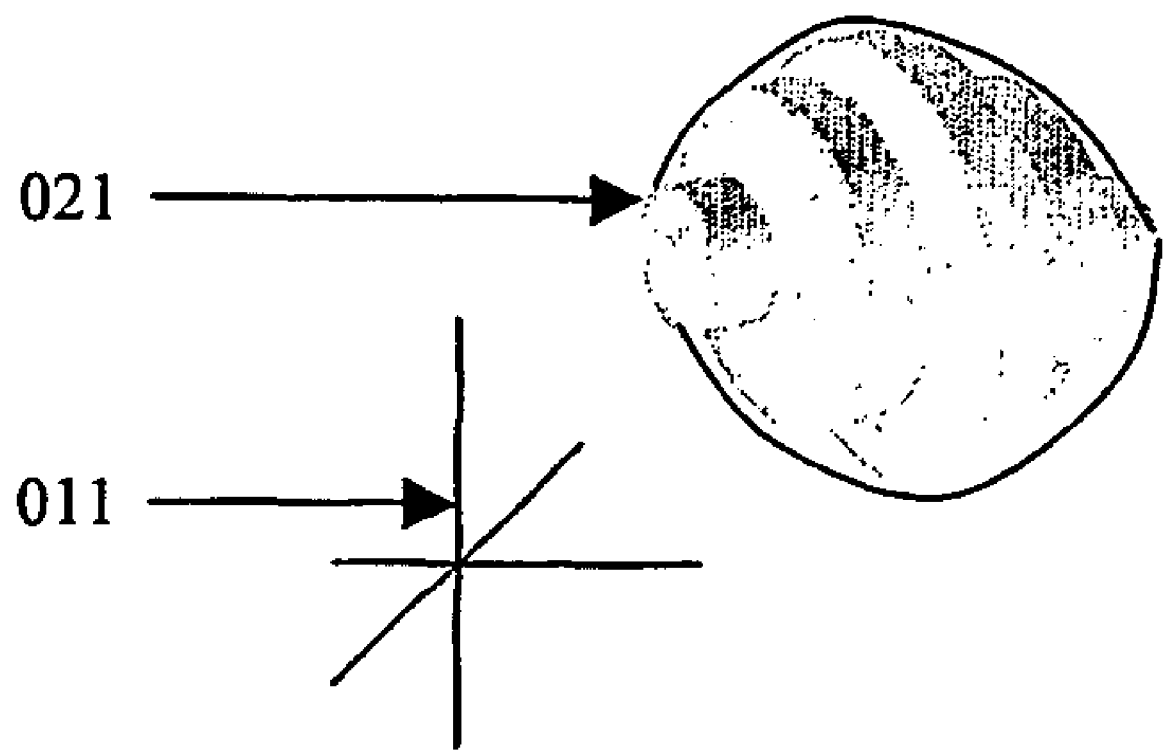
FIG. 13 is a three-dimensional rendering of the outline of the image prepared from the lesion contours as illustrated in FIG. 12.

When the ultrasound three-dimensional image data 031 and the diagnostic three-dimensional image data 027 are combined, contours 022 of the outer surface of the lesion 010 can be defined in arbitrarily selected planes within the ultrasound three-dimensional image data 031 or diagnostic three-dimensional image data 027 (FIG. 12) and displayed at their correct location within the ultrasound three-dimensional image data 031 or the diagnostic three-dimensional image data 027. These contours 022 can be used to perform three-dimensional rendering 021 of the lesion within the diagnostic three-dimensional image data 027 (FIG. 13). In this manner, the lesion 010 is (1) localized and defined with respect the absolute coordinate reference system 011 of the diagnostic device 002 and (2) localized, defined and visualized within the diagnostic three-dimensional image data 027. Because of (1) and (2) above, a radiation treatment plan can be designed in a conventional manner to deliver the necessary radiation to the lesion 010. This is so even if the lesion 010 may not have been completely visualized by the image or images 023 acquired with the diagnostic imaging device 002 or alternately, by the ultrasound device 005. However, the combination of the two creates a more accurate picture of the tumour 010. Thereafter, a radiation treatment plan, such as for example a conformal plan, whereby the shape of the radiation beam will conform to the spatial contour or outline 022 of the lesion may be designed.

In addition, if a healthy organ 010 is localized and outlined with the above described procedure, the radiation treatment plan will preferably be designed to avoid excessive radiation damage to the organ 010. The ultrasound three-dimensional image data 031, the diagnostic three-dimensional image data 027, the contours 022 of the outer surface of the lesion 010 and the three-dimensional rendering 021 of the lesion 010 may then be transferred from the workstation 031 as illustrated in FIG. 1 to a computer or a workstation 014 in the control area of the radiation therapy device 003, also illustrated in FIG. 1, to serve as reference data for the verification of the treatment position of the turnout or lesion or organ 011 before the radiation treatment session.

It is understood that the above described comparison between a diagnostic image 027 and the ultrasound image 031 is not a necessary step of the hereinafter described method. Thus, in accordance with an additional embodiment of the present invention, and in order to avoid the above described type II failures, it may be necessary to compare a tumour 010 immediately prior to the beginning of the radiation treatment, with the same tumour 010 as defined during the treatment plan. This is to ensure that any change in the tumour, i.e. its size, location, orientation etc. . . . may be accounted for, through a change in the treatment plan if necessary. In order to accomplish this, an ultrasound of the tumour 010 may be taken during the treatment plan, the whole as described above, using ultrasound equipment 008 and 005. It is understood that the use of an absolute coordinate system 011 in conjunction with the taking of the ultrasound during the diagnostic phase may be required in order to assign absolute coordinates to said tumour 010.

Figure 14:
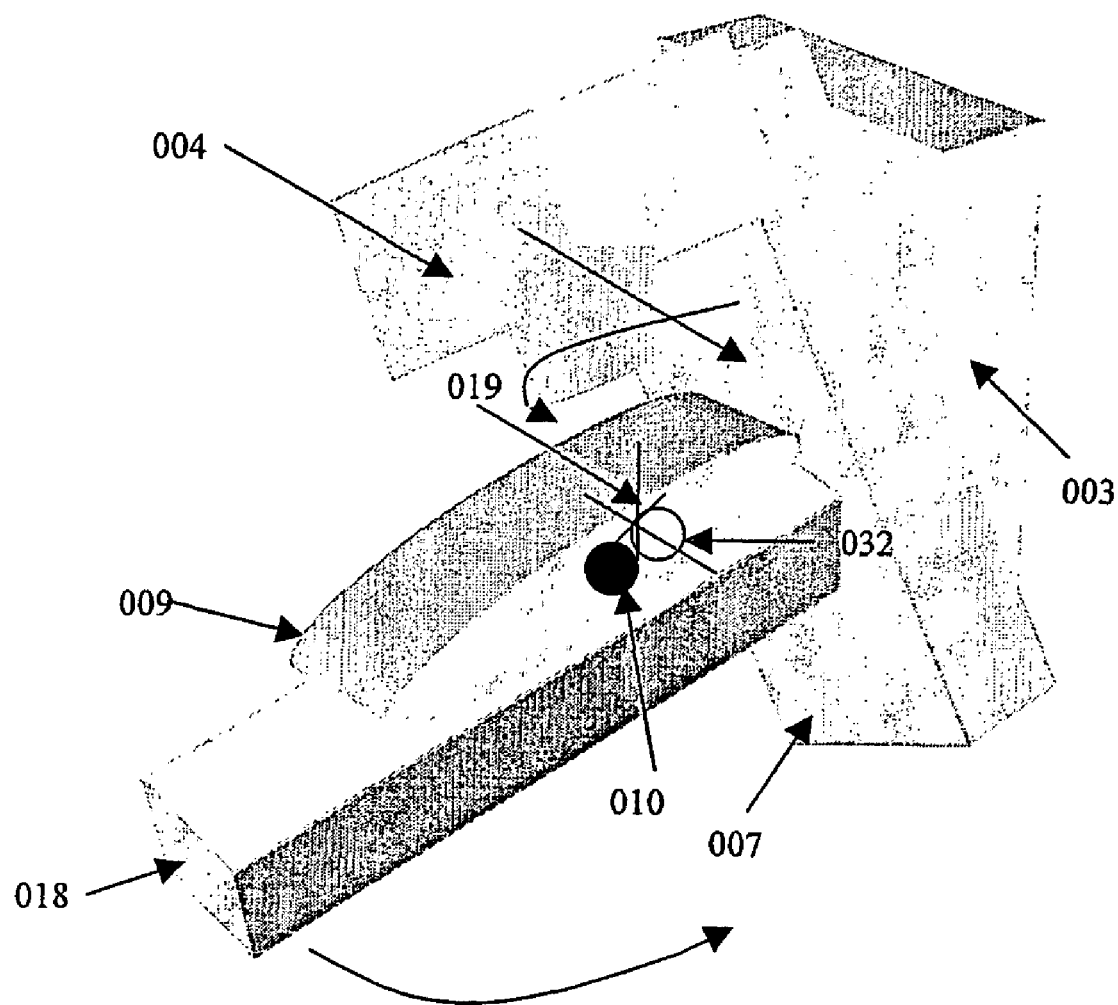
FIG. 14 is a perspective view of a conventional radiotherapy treatment device, or linear accelerator including a rotatable couch, collimator and gantry.

Before the radiation treatment session begins, the verification of the tumour or lesion or organ 010 position may proceed in the following manner. With reference to FIG. 14, the patient 009 having a tumour or a lesion or an organ of interest 010 may be disposed on the treatment table 018 of the conventional therapy device 003 hereafter referred to as a linear accelerator. It is understood that the method herein described may be used with any known or future radiation therapy device, or with any other type of therapy apparatus. The same patient has had in the past, such as in the immediate past, an ultrasound performed in order to determine the size, shape and orientation of the tumour 010 during the diagnostic phase, the whole as described above. During said ultrasound, an absolute coordinate (X, Y, Z) was assigned to said tumour. As depicted in FIG. 14, at the time of the treatment session, in the therapy room, the position (possibly including orientation and shape), in other words, the absolute coordinates of the tumour or lesion or organ 010 of the patient on the therapy table 018 will undoubtedly be different than the absolute coordinates of the tumour 010 as assigned during the previous diagnostic phase. This may be due to a variety of factors, including different sizes and shapes of the machines involved, different positioning of the patient 009, and the fact that the tumour 010 itself may have grown, shrunk, or moved.

It is therefore important to be able to account for, and compensate for this difference in position of the tumour 010. In order to do so, a common absolute reference frame or system, i.e. common to the ultrasound device 008 and to the therapy device 003 must be devised, to be able to correlate positions between a tumour 010 as identified by the ultrasound imaging device 008, and the same tumour 010 identified by ultrasound prior to being treated by the linear accelerator 003, which linear accelerator is probably situated in a different physical location.

Figure 17:
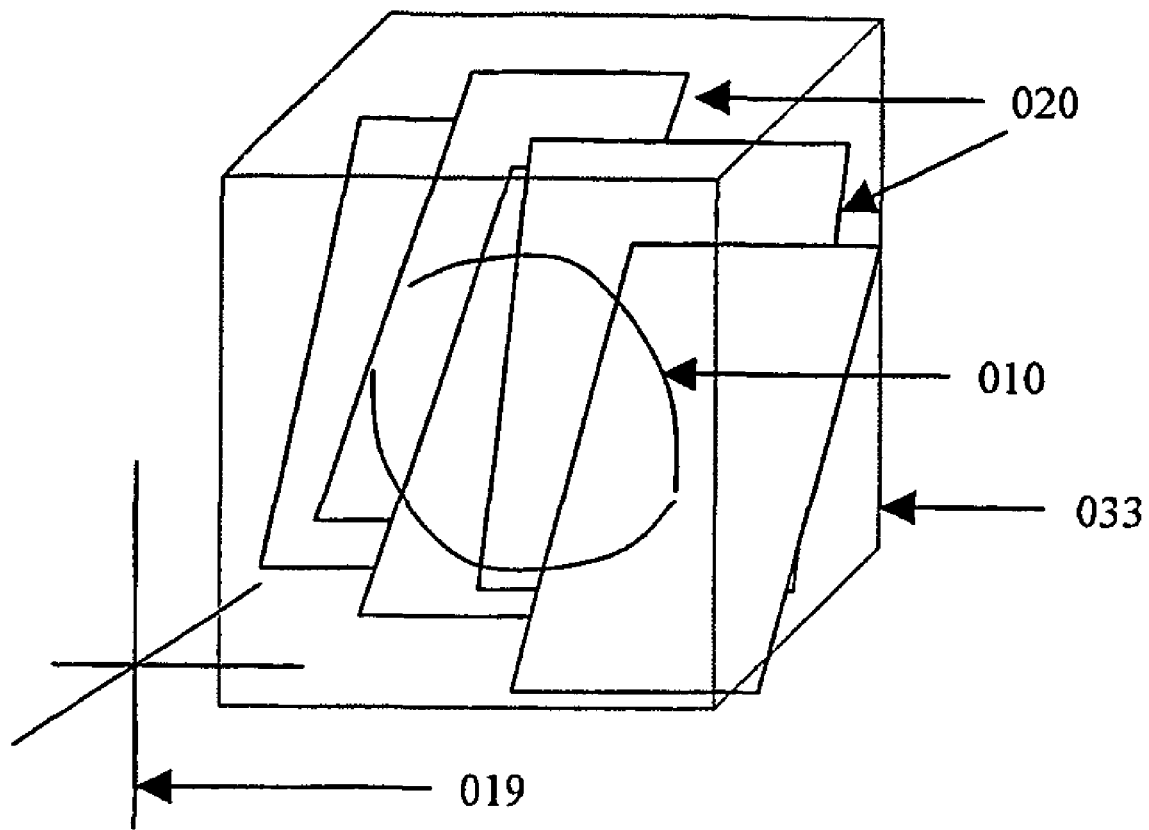
FIG. 17 is a representation of the three-dimensional ultrasound image data reconstructed from the multiple ultrasound images acquired in the room of the therapy device and depicted in FIG. 16.

This may be accomplished through the use of a similar measurement system as described above, which system may, for example, comprise lasers disposed on the walls or the ceiling of the treatment room (019, FIG. 1). The measurement system used in the diagnostic room with the ultrasound 008 and 005 may be the same as the measurement system used in the treatment room, although not strictly necessary. However, both systems must be calibrated so as to give a reference frame which is common to both the diagnostic ultrasound device 008 and the therapy device 003. As a result, the absolute coordinate reference system 011 of the ultrasound diagnostic device 005 and the absolute coordinate system 019 of the therapy device 003 (as illustrated in FIG. 17) may give coordinates which are common to both, and which can be correlated. As a result, the intended treatment position 032 (possibly including orientation) of the lesion 010 may be calculated from the spatial coordinates and extent of the lesion 010 determined previously by the ultrasound imaging device 002 with the localization and definition method described earlier and illustrated in FIG. 2 to FIG. 13.

Typically, in the process of treatment planning a 4×4 transformation matrix T may be determined which when applied to the patient by mechanical motions of the therapy device table 018, of the treatment device collimator 004 as well as of the treatment device gantry 007 disposes the tumour or lesion or organ 010 in the desired treatment position. If the absolute coordinate reference system 011 of the ultrasound diagnostic device 002 and the absolute coordinate system 019 of the therapy device 003 are not identical, a predefined transformation matrix or coordinate transformation may be used between the two to correlate coordinates of a tumour 010 in one system with the coordinates in the other.

Figure 15:
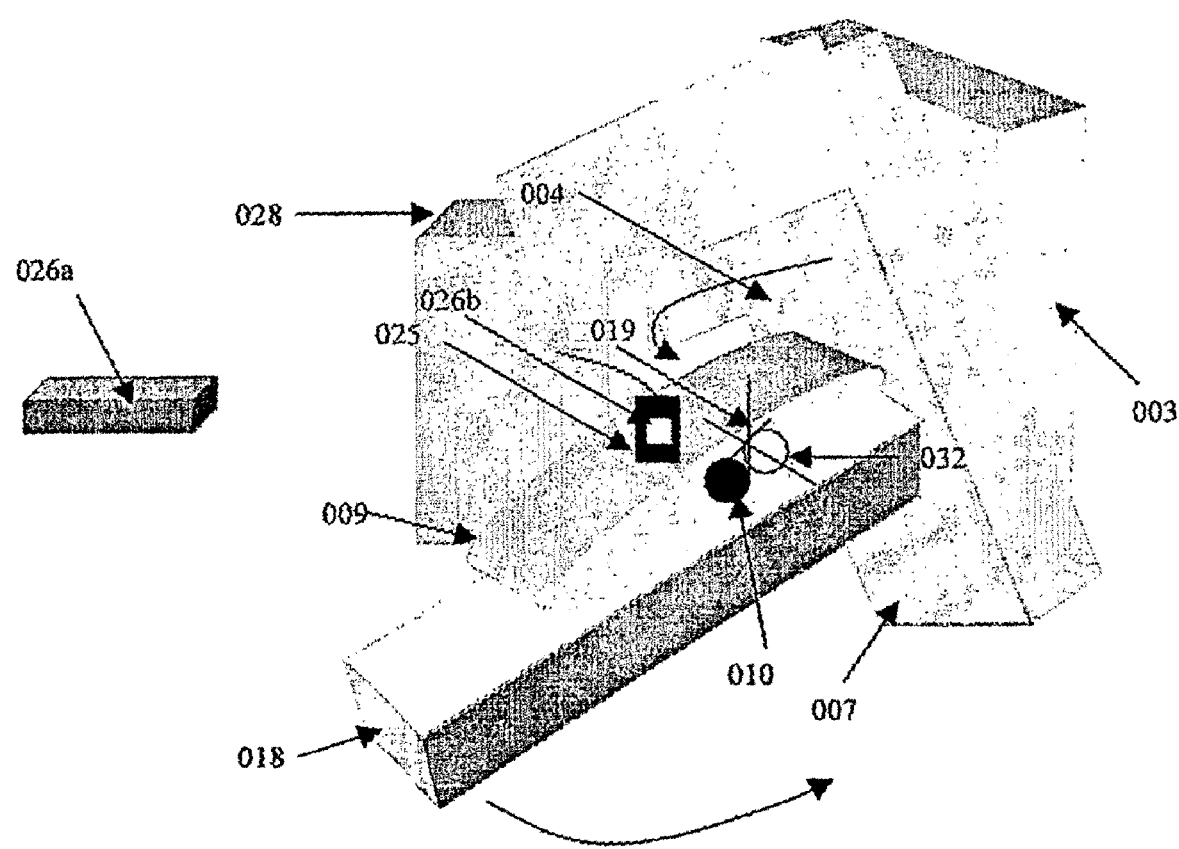
FIG. 15 is a perspective schematic view of the linear accelerator including a means for generating an ultrasound image of the lesion within the patient's body.

As a first step towards the verification of the intended treatment position, localization and definition of the actual position of the tumour, or lesion or organ 010 is performed in the room of the conventional radiotherapy device 003 similarly to the localization and definition of the tumour, or lesion or organ 010 performed in the room of the ultrasound diagnostic device 002. A means 028 (FIG. 15) for generating at least one ultrasound image 020 of the lesion 010 (FIG. 15) is disposed in the therapy room, as depicted in FIG. 15. Preferably the means 028 for generating at least one ultrasound image 020 utilizes a conventional, commercially available ultrasound probe 025 (FIG. 15).

Figure 16:
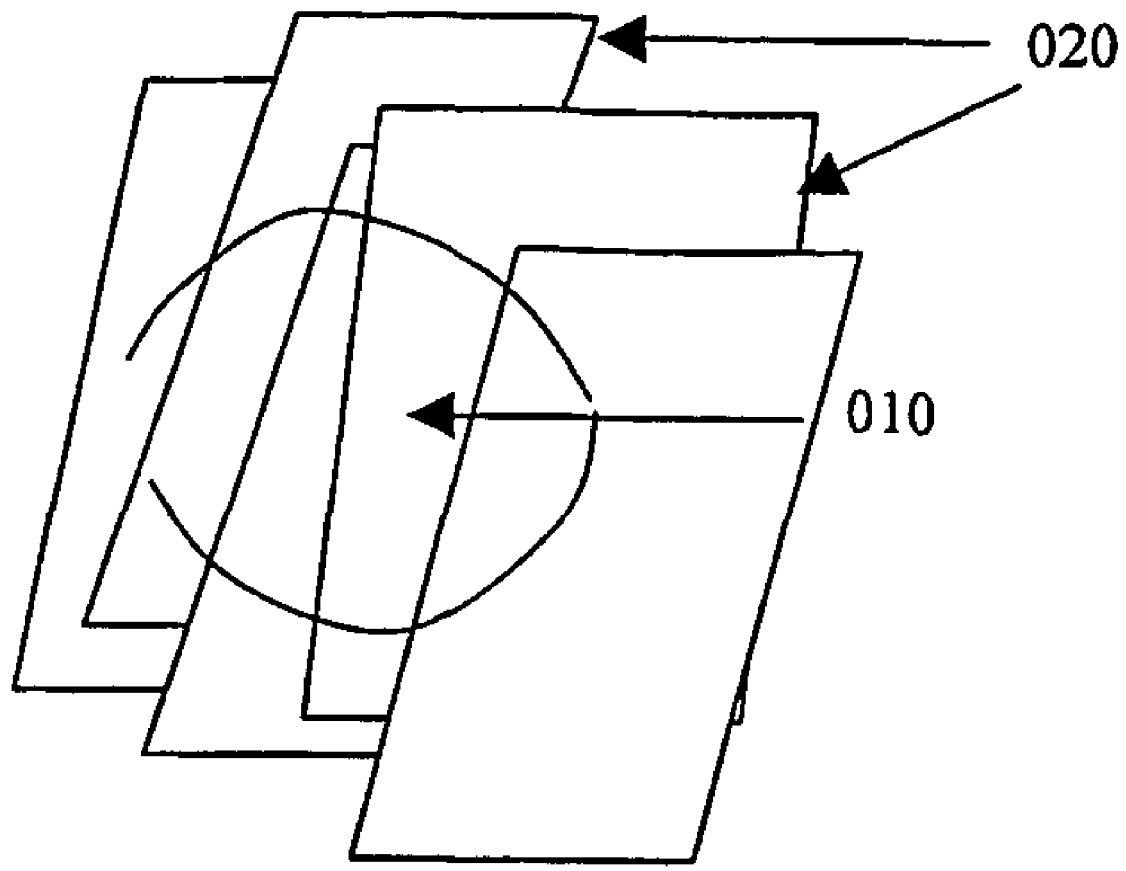
FIG. 16 is a view indicating multiple ultrasound images being taken of a lesion with the ultrasound imaging device of FIG. 15.

The ultrasound probe 025 is brought in contact with the patient body 009 (FIG. 15) in order to generate an ultrasound image or images 020 of the tumour or lesion or organ 010 (FIG. 16). By moving or rotating the ultrasound probe 025, a plurality of ultrasound images 020 (FIG. 16) of the tumour or lesion or organ 010 may be acquired. In FIG. 16, the lesion 010 is shown disposed within the plurality of ultrasound images 020 with the plane of each ultrasound image representative of the orientation of the ultrasound probe 025 at the time of the ultrasound image acquisition. From the plurality of ultrasound images 020 a reconstruction of the three-dimensional volume or picture 033 (FIG. 17) of the ultrasound data is performed in the absolute coordinate system 019 of the therapy device 003. It is to be noted that, depending on the size of the reconstructed volume 033 there may be location in the periphery of reconstructed volume 033 for which ultrasound data are not available.

In order to accurately reconstruct the three-dimensional volume 033 of the ultrasound data from the plurality of ultrasound images 020, for each acquired ultrasound image 020, the orientation and the position (hereafter referred to as the orientation) of the ultrasound probe 025 with respect to the absolute coordinate system 019 of the therapy device 003 must be known. A means 026a, 026b for indicating the geometric orientation of the ultrasound probe 025 may be disposed in the room of the therapy device 003 as shown in FIG. 15. Any conventional position sensing system can be used as means 026a, 026b to determine the position and the orientation of the ultrasound probe 025 with respect to the coordinate system 019 of the therapy device 003, the whole as more fully described above. Although not necessarily identical to the system described above with respect to the diagnostic ultrasound device 008, it may be convenient for both systems to be the same. It is to be noted that neither the ultrasound probe 025 nor the means 026a, 026b for indicating the geometric orientation of the ultrasound probe 025 have to be fixed to the table 018 of the therapy device 003.

Figure 18:
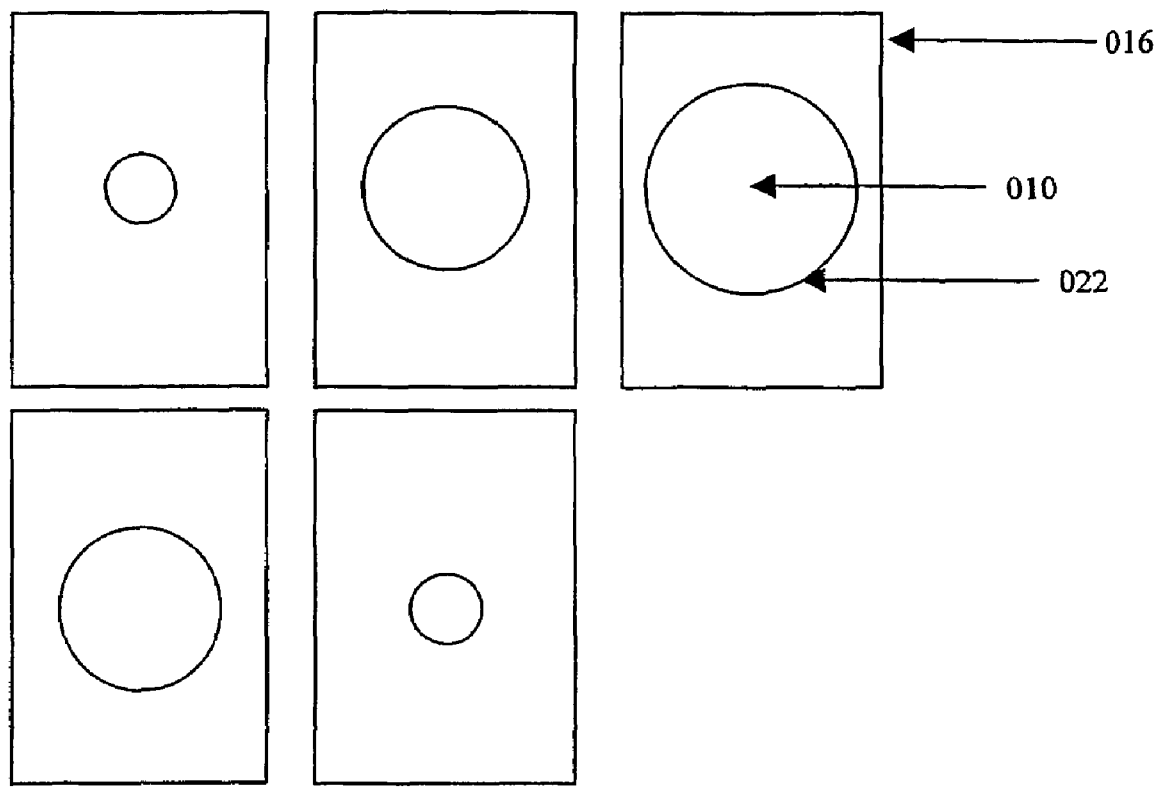
FIG. 18 is a representation of several two-dimensional ultrasound images with the lesion of FIG. 17 having its outer surface outlined.
Figure 19:
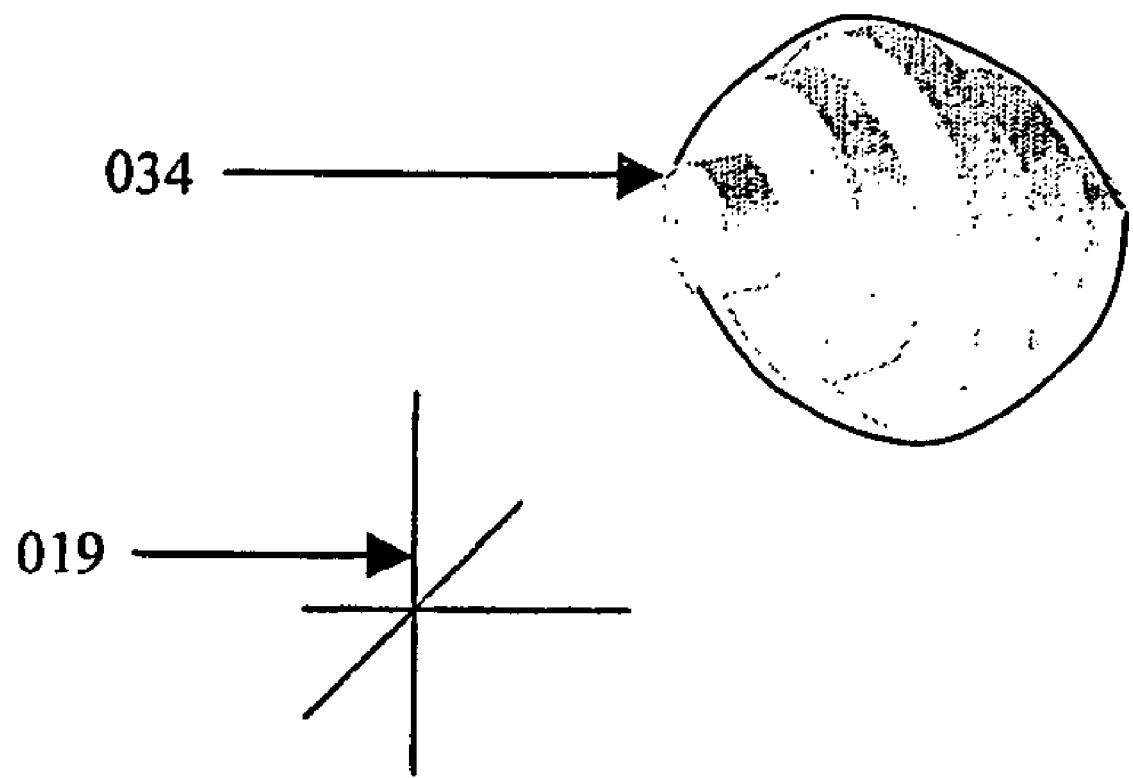
FIG. 19 is a three-dimensional rendering of the outline of the image prepared from the plurality of images from FIG. 18.

The means 026a-026b for indicating the geometric orientation of the ultrasound probe 025 are aligned with or as known in the art, calibrated to the absolute coordinate reference system 019 of the therapy device 003. Because of this alignment or calibration, for any point or feature from the plurality of ultrasound images, the coordinates (A, B, C) of any point, i.e. tumour 010 in the absolute coordinate system 019 of the therapy device 003 are known. With this knowledge, the value of the ultrasound image data for each point within the reconstructed volume 033 (FIG. 17) can be determined by interpolating algorithms known to those of ordinary skill in the art. Furthermore, for any point or feature within the volume of ultrasound image data 033 (FIG. 17) the coordinates (X, Y, Z) in the absolute coordinate system 019 of the therapy device 003 are known. Thus the localization of the tumour or lesion or organ 010 as depicted by the three-dimensional ultrasound image data 033 (FIG. 17) is complete. Furthermore, contours 024 (FIG. 18) of the outer surface of the lesion 010 can be defined in arbitrary planes within the ultrasound three-dimensional image data 033 (FIG. 17). These contours 024 can be used to properly perform three-dimensional rendering 034 (FIG. 19) of the lesion in the coordinate system 019 of the therapy device 003.

Figure 20:
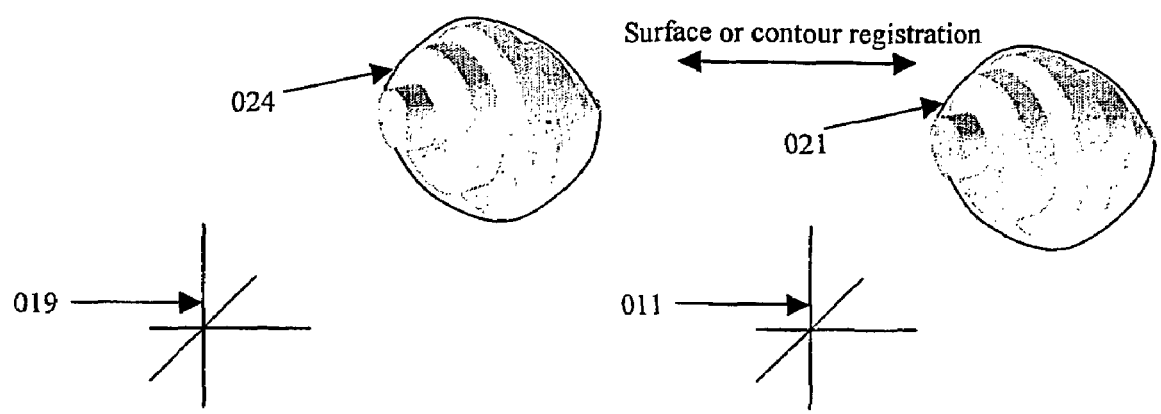
FIG. 20 is a representation of the process of determining the necessary corrections in the treatment setup (table position, collimator and gantry rotation) prior to a treatment session based on contour or surface registration.

Once the tumour or lesion or organ 010 is localized in the room of the therapy device 003, the necessary adjustments of the treatment table 018 position, of the treatment device collimator 004 rotation as well as of the treatment device gantry 007 rotation can be performed by either of the following two methods. With reference to FIG. 20, the first method establishes a coordinate transformation (4×4 transformation matrix) R between the absolute coordinate system 011 of the ultrasound diagnostic device 002 and the coordinate system 019 of the therapy device 003 by superimposing or matching of the three-dimensional surface 022 or contours 021 of the lesion 010 as outlined within the three-dimensional ultrasound localization data 031 acquired with the ultrasound diagnostic device 002 prior to the treatment plan to the three-dimensional surface 034 or contours 024 of the lesion 010 as outlined within the three-dimensional ultrasound localization data 033 acquired by the ultrasound device 025 and 028 in the therapy device 003, Conventional methods for contour and surface matching may include chamfer matching and "top-and-hat" least square distance matching, as well as any other required or desired method.

Figure 21:
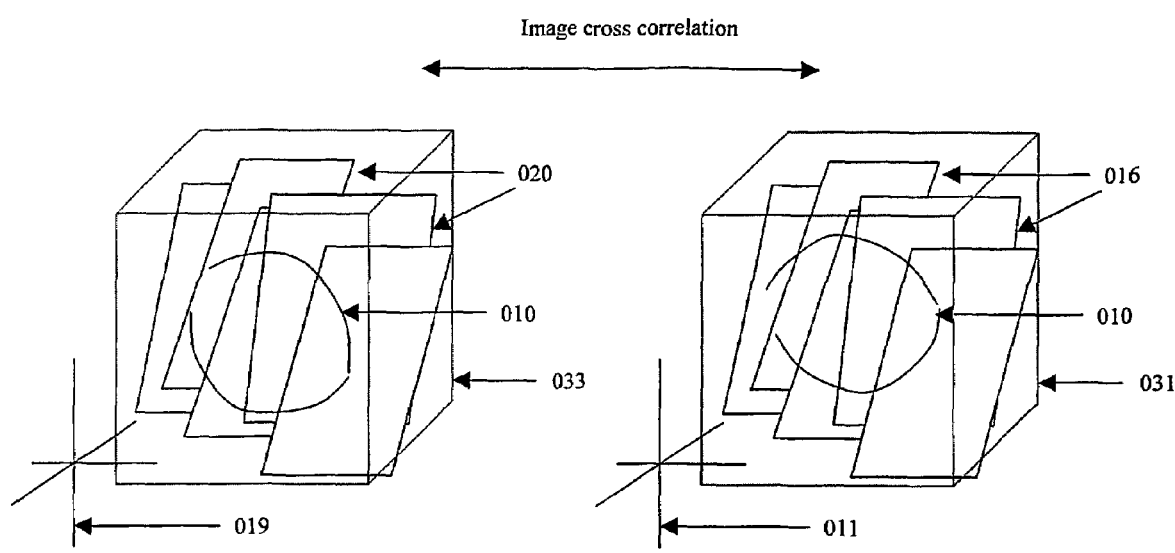
FIG. 21 is a representation of the process of determining the necessary corrections in the treatment setup (table position, collimator and gantry rotation) prior to a treatment session based on image cross-correlation.

An alternative method for the establishment of the coordinate transformation R between the absolute coordinate system 031 of the ultrasound diagnostic device 002 and the coordinate system 019 of the therapy device 003, which does not rely on predefined contours or surfaces is illustrated in FIG. 21. In this alternative, the image cross correlation is performed between the reconstructed three-dimensional ultrasound localization data 033 acquired in the room of the therapy device 003 before the treatment session and the three-dimensional ultrasound localization data 031 acquired in the room of the diagnostic device 002 prior to the design of the treatment plan. The coordinate transformation is selected to be the one which produces the highest peak of the correlation value between the two three-dimensional data sets 033 and 031. The determination of the necessary adjustments of the treatment table 018 position, of the treatment device collimator 004 rotation as well as of the treatment device gantry 007 rotation is then performed by a decomposition of the 4×4 transformation matrix $TR^{-1}$ by algorithms known to those of ordinary skill in the art. It is to be noted that after the establishment of the coordinate transformation R between the absolute coordinate system 011 of the ultrasound diagnostic device 002 and the coordinate system 019 of the therapy device 003 by either of the above said two methods, adjustments other than the above said adjustments of the treatment table 018 position, of the treatment device collimator 004 rotation as well as of the treatment device gantry 007 rotation can be undertaken. These may range from simple modifications of the initially intended radiation beam shapes to change in the beam intensities and even a completely new treatment plan with different beam arrangements. These adjustments are calculated with software running on the workstation 014 and executed by the therapy device controller 015 which is interfaced to the therapy device 003 and treatment table controller 012 as illustrated in FIG. 1.

While particular preferred embodiments of the invention have been shown and described, it will be obvious to those of skill in the art that changes and modifications can be made without departing from the spirit and the scope of the invention as set forth in the claims. Accordingly, the invention is limited only by the scope of the appended claims.

We claim:

1. A method for spatially localizing a lesion for the purposes of radiation treatment planning in a treatment planning session comprising the steps of:
   a) generating, in the treatment planning session, one or more diagnostic images of said lesion in an absolute coordinate reference system using a non-ultrasound diagnostic imaging device;
   b) assigning said lesion on said diagnostic image a first set of three-dimensional coordinates in the absolute coordinate reference system;
   c) generating, in the treatment planning session, one or more ultrasound images of said lesion in the absolute coordinate reference system using an ultrasound device;
   d) assigning said lesion on said ultrasound images a second set of three-dimensional coordinates in said absolute coordinate reference system;
   e) fusing said diagnostic image and said ultrasound images in registration using the first and second sets of three-dimensional coordinates of the absolute coordinate reference system so as to obtain an enhanced image of the lesion; and
   f) developing a radiation treatment plan based, at least in part, on the fused images.

2. The method of claim 1 wherein said absolute coordinate reference system is determined through the use of a means for establishing an absolute coordinate reference system.

3. The method of claim 2 wherein said means for establishing an absolute coordinate reference system comprises at least one laser.

4. The method of claim 3 wherein said absolute coordinate reference system is independent of said diagnostic imaging device.

5. The method of claim 3 wherein said absolute coordinate reference system is independent of said ultrasound device.

6. The method of claim 1 wherein said one or more diagnostic images are combined to form a three-dimensional image, wherein said lesion has a plurality of three-dimensional coordinates.

7. The method of claim 1 wherein said one or more ultrasound images are combined to form a three-dimensional image, wherein said lesion has a plurality of three-dimensional coordinates.

8. The method of claim 1 further including the step of drawing contours of the outer surface of the lesion on said diagnostic images by drawing the contours of the outer surface of the lesion on the one or more ultrasound images.

9. The method of claim 1 wherein said diagnostic image and said one or more ultrasound images are generated at substantially the same time.

10. The method of claim 1 wherein a plurality of the diagnostic images and a plurality of the ultrasound images are generated, each plurality of images representing slices of the lesion, the diagnostic images and the ultrasound images being registered into a plurality of composite images each representing a slice of the lesion.

11. The method of claim 1 further comprising:
    g) during a treatment delivery session subsequent to the treatment planning session, generating one or more ultrasound images of said lesion;
    h) comparing the one or more ultrasound images generated during the treatment planning session with the one or more ultrasound images generated during the treatment delivery session; and
    i) treating the lesion with radiation based at least in part on the comparison.

12. The method of claim 11 further comprising adjusting the treatment plan based at least in part on the comparison.

13. The method of claim 1 further comprising:
    g) during a treatment delivery session subsequent to the treatment planning session, generating one or more ultrasound images of said lesion using an ultrasound device;
    h) assigning said lesion a third three-dimensional coordinate using an absolute coordinate reference system;
    i) fusing ultrasound images generated during the treatment planning session and ultrasound images generated during the treatment delivery session using first and third three-dimensional coordinates so as to compare the images; and
    j) treating the lesion with radiation based at least in part on the comparison.

14. A system for spatially localizing a lesion for the purposes of radiation treatment planning comprising:
    a) a diagnostic imaging device, selected from the group comprising an MRI scanner, a PET scanner, and a CT scanner, for generating at least one diagnostic image of said lesion in an absolute coordinate system;
    b) an ultrasound device for generating at least one ultrasound image of said lesion in the absolute coordinate system, the diagnostic and ultrasound images thereby being in registration at the time of generation;
    c) a means for assigning to said lesion (i) a first set of three-dimensional coordinates in the absolute coordinate system on said diagnostic image, and (ii) a second set of three-dimensional coordinates in the absolute coordinate system on said ultrasound image;
    d) a means for fusing said diagnostic image and said ultrasound image in the absolute coordinate reference system so as to obtain an enhanced image of said lesion; and
    e) a means for facilitating the development of a radiation treatment plan based at least in part on the fused images.

15. The system of claim 14 wherein said ultrasound device comprises an ultrasound probe, wherein said ultrasound probe comprises a positioning system configured so as to allow the position and orientation of each ultrasound image to be known, such that a lesion on said ultrasound image may be assigned a three-dimensional coordinate in said absolute coordinate reference system.

* * * * *